United States Patent
Paul et al.

(10) Patent No.: US 7,311,704 B2
(45) Date of Patent: Dec. 25, 2007

(54) SPRING-TIP, FLEXIBLE ELECTRODE CATHETER FOR TISSUE ABLATION

(75) Inventors: Saurav Paul, Minnetonka, MN (US); Kedar Ravindra Belhe, Minnetonka, MN (US); Hong Cao, Savage, MN (US); John Avi Roop, Crystal, MN (US); Chou Thao, Brooklyn Park, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 379 days.

(21) Appl. No.: 10/856,904

(22) Filed: May 27, 2004

(65) Prior Publication Data

US 2005/0267332 A1    Dec. 1, 2005

(51) Int. Cl.
*A61B 18/18* (2006.01)
(52) U.S. Cl. .................................. 606/41; 607/101
(58) Field of Classification Search ............ 606/41, 606/45–50; 607/101, 102
See application file for complete search history.

(56) References Cited

U.S. PATENT DOCUMENTS

| | | |
|---|---|---|
| 4,358,699 A | 11/1982 | Wilsdorf |
| 4,415,635 A | 11/1983 | Wilsdorf et al. |
| 5,246,438 A | 9/1993 | Langberg |
| 5,334,193 A | 8/1994 | Nardella |
| 5,433,708 A | 7/1995 | Nichols et al. |
| 5,542,928 A | 8/1996 | Evans et al. |
| 5,582,609 A | 12/1996 | Swanson et al. |
| 5,676,662 A | 10/1997 | Fleischhacker et al. |
| 5,676,693 A | 10/1997 | LaFontaine |
| 6,015,407 A | 1/2000 | Rieb et al. |
| 6,168,594 B1 | 1/2001 | LaFontaine et al. |
| 6,241,722 B1 | 6/2001 | Dobak et al. |
| 6,402,745 B1 | 6/2002 | Wilk |
| 6,780,180 B1* | 8/2004 | Goble et al. ............... 606/41 |
| 6,837,888 B2* | 1/2005 | Ciarrocca et al. .......... 606/41 |
| 2001/0024735 A1 | 9/2001 | Kuhlmann-Wilsdorf et al. |
| 2002/0095151 A1* | 7/2002 | Dahla et al. ............... 606/41 |
| 2004/0254572 A1* | 12/2004 | McIntyre et al. .......... 606/41 |
| 2005/0159740 A1* | 7/2005 | Paul et al. ................. 606/41 |
| 2005/0159741 A1* | 7/2005 | Paul et al. ................. 606/41 |
| 2005/0267458 A1* | 12/2005 | Paul et al. ................. 606/41 |
| 2005/0267467 A1* | 12/2005 | Paul et al. ................. 606/41 |

* cited by examiner

*Primary Examiner*—Michael Peffley
(74) *Attorney, Agent, or Firm*—Heimbecher & Assoc., LLC

(57) ABSTRACT

A spring-tip, flexible electrode, and a method for using that electrode for tissue ablation, are disclosed. The spring-tip, flexible electrode comprises an enshrouded flexible electrode (e.g., an enshrouded plurality of flexible brush filaments or bristles) for applying ablative energy (e.g., RF energy) to target tissue during the formation of spot or continuous linear lesions. The spring of the spring tip may comprise compressible coils, compressible mesh, or compressible bellows, among other things. The spring provides axial suspension and is capable of axial compression and extension, and is flexible enough for deflection and bending. The axial suspension of the spring tip facilitates the desired contact between the electrode and the tissue surface. A shielded, spring-tip, flexible electrode is also disclosed, and includes a flexible nipple or shield. The spring-tip, flexible electrode facilitates enhanced tissue contact in difficult environments (e.g., during ablation of a contoured or trabeculated surface inside a beating heart) since the flexible electrode readily conforms to surface contours while the bending stress of the spring enhances the contract pressure on the tissue.

18 Claims, 25 Drawing Sheets

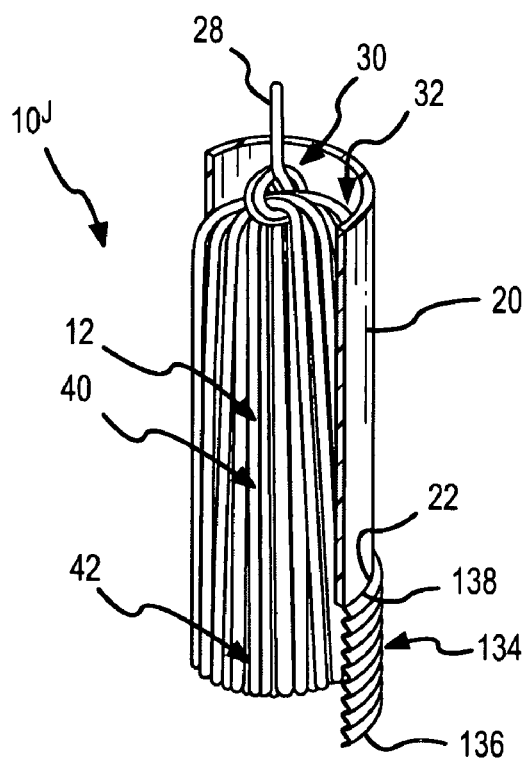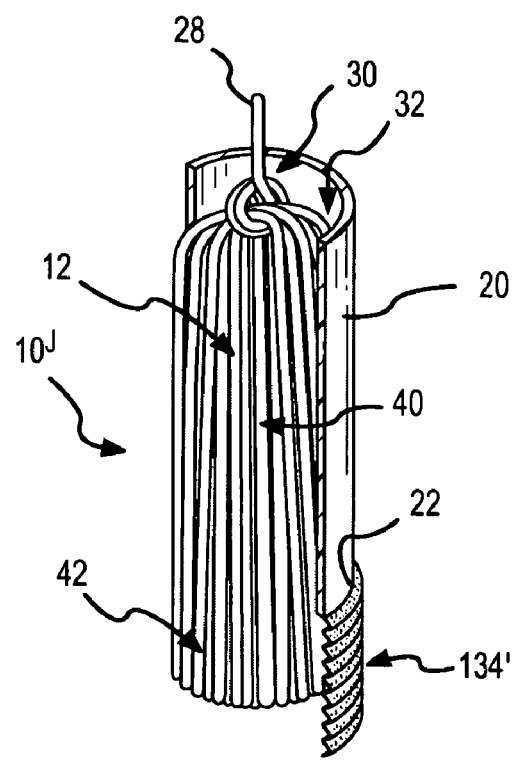
FIG.31  FIG.32
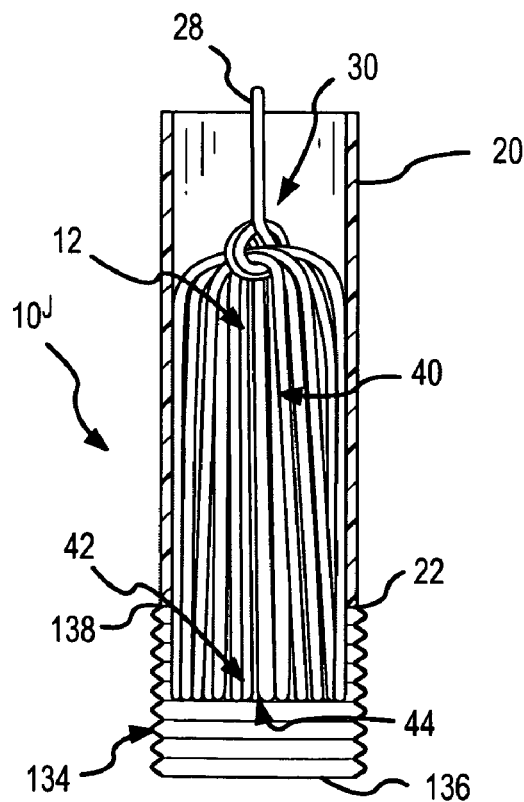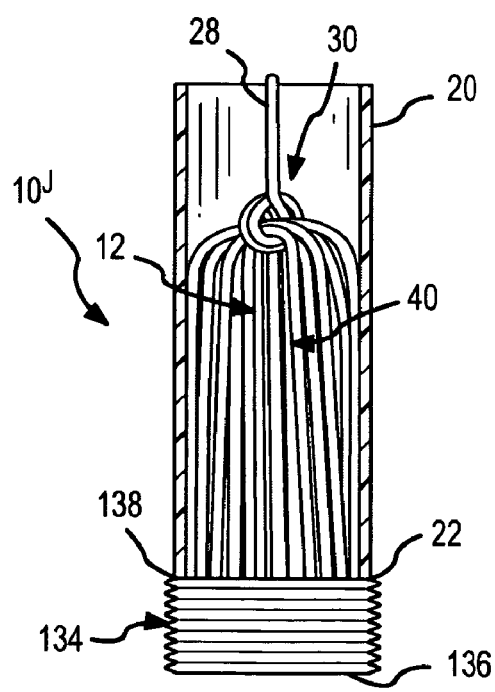
FIG.33  FIG.34

SPRING-TIP, FLEXIBLE ELECTRODE CATHETER FOR TISSUE ABLATION

BACKGROUND OF THE INVENTION a. Field of the Invention

The instant invention is directed toward a spring-tip, flexible electrode catheter and a method for using the spring-tip, flexible electrode catheter for tissue ablation. In particular, the spring-tip flexible electrode catheter of the present invention comprises an enshrouded flexible electrode (e.g., a plurality of flexible brush filaments or bristles) for applying ablative energy (e.g., RF energy) to target tissue during the formation of spot or continuous linear lesions.

b. Background Art

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable atrial fibrillations may be lessened or eliminated. "Sufficiently deep" lesions means transmural lesions in some cardiac applications.

Several difficulties may be encountered, however, when attempting to form adequately-deep lesions at specific locations using some existing ablation electrodes. For example, when forming lesions with RF energy, high temperature gradients are often encountered in the vicinity of the electrode. At the edges of some existing electrodes are regions of very high current density, leading to large temperature gradients and hot spots. These "edge effects" may result in the formation of undesirable coagulum and charring of the surface tissue. For example, undesirable coagulum may begin to form when blood reaches around 80° C. for an appreciable length of time, and undesirable tissue charring and desiccation may be seen when tissue reaches around 100° C. for an appreciable length of time. There two types of undesirable coagulum: coagulum that adheres to and damages the medical device; and coagulum blood clots or curds that may enter a patient's bloodstream, possibly resulting in other health problems for the patient. Charring of the surface tissue may also have deleterious effects on a patient.

As the temperature of the electrode is increased, the contact time required to form an adequately-deep lesion decreases, but the likelihood of charring surface tissue and forming undesirable coagulum increases. As the temperature of the electrode is decreased, the contact time required to form an adequately-deep lesion increases, but the likelihood of charring surface tissue and forming undesirable coagulum decreases. It is, therefore, a balancing act trying to ensure that tissue temperatures are adequately high for long enough to create deep lesions, while still preventing or minimizing coagulum formation and/or charring of the surface tissue. Active temperature control may help, but the placement of thermocouples, for example, is tricky and setting the RF generator for a certain temperature becomes an empirical exercise as actual tissue temperatures are generally different from those recorded next to the electrode due to factors such as convection and catheter design.

Another difficulty encountered with existing ablation electrodes is how to ensure adequate tissue contact. Current techniques for creating continuous linear lesions in endocardial applications include, for example, dragging a conventional catheter on the tissue, using an array electrode, or using pre-formed electrodes. All of these devices comprise rigid electrodes that do not always conform to the tissue surface, especially when sharp gradients and undulations are present, such as at the ostium of the pulmonary vein in the left atrium and the isthmus of the right atrium between the tricuspid valve and the inferior vena cava. Consequently, continuous linear lesions are difficult to achieve. When forming lesions in a heart, the beating of the heart further complicates matters, making it difficult to keep adequate contact between the electrode and the tissue for a sufficient length of time to form a desired lesion. With a rigid electrode, it can be quite difficult to maintain sufficient contact pressure until an adequate lesion has been formed. This problem is exacerbated on contoured or trabeculated surfaces. If the contact between the electrode and the tissue cannot be properly maintained, a quality lesion is unlikely to be formed.

Catheters based upon a virtual electrode may address some of the difficulties, but these catheters often require high flow rates of conductive fluid (e.g., typically around 70 milliliters per minute) to maintain effective cooling for high-power RF applications. The introduction of a large amount of conductive fluid into a patient's bloodstream may have detrimental effects on the patient.

Thus, there remains a need for an ablation catheter that address these issues with the existing designs and that permits the formation of uniform, transmural spot and continuous linear lesions on smooth or contoured surfaces.

BRIEF SUMMARY OF THE INVENTION

It is desirable to be able to form adequately-deep spot or continuous linear lesions in tissue while reducing the formation of undesirable coagulum and charring of the surface tissue, while applying a reasonable amount of RF energy, while mitigating electrode-tissue contact problems, and/or while reducing the amount of conductive fluid (e.g., isotonic saline) possibly entering a patient's bloodstream during the procedure. The present invention is an improved ablation electrode. One of the ways in which the present invention improves catheter-tissue contact is by allowing catheter placement at variable incidence angles of contact in trabeculated regions of the myocardium.

In one form, the present invention comprises a spring-tip, flexible electrode catheter including a catheter sheath having a distal end; a flexible electrode extending from the distal end of the catheter sheath; and a spring at the distal end of the catheter sheath, wherein the spring enshrouds at least a portion of the flexible electrode. The flexible electrode may be electrically conductive, and the catheter may further comprises a primary conductor operatively connected to the flexible electrode. The spring may be, for example, a round-wire, coil spring; an outwardly-tapering, round-wire, coil spring; an inwardly-tapering, round-wire, coil spring; a flat-wire, coil spring; an outwardly-tapering, flat-wire, coil spring; an inwardly-tapering, flat-wire, coil spring; a compressible mesh; an outwardly-tapering, compressible mesh; an inwardly-tapering, compressible mesh; a compressible bellows; an outwardly-tapering, compressible bellows; an inwardly-tapering, compressible bellows.

In another form, the present invention comprises a booted, spring-tip, flexible electrode catheter comprising an inner sheath having an inner sheath distal end and defining an inner sheath lumen, wherein the inner sheath distal end supports a mechanical interface; an intermediate sheath having an intermediate sheath distal portion and defining an intermediate sheath lumen; an outer sheath having an outer sheath distal end and defining an outer sheath lumen; a flexible electrode supported by the mechanical interface; a spring at the inner sheath distal end, wherein the spring has a distal portion, and wherein the spring enshrouds at least a portion of the flexible electrode; and a flexible boot having a flexible boot distal edge, wherein the flexible boot covers the distal portion of the spring, and wherein the flexible electrode extends from the flexible boot distal edge.

In yet another form, the present invention comprises a spring-tip, flexible electrode catheter for ablating target tissue inside a body cavity. The catheter comprises an outer sheath having a distal end; a conforming electrode adapted to apply ablative energy to the target tissue, the conforming electrode comprising an embedded portion and an exposed portion, wherein the exposed portion has a distal end, wherein a working surface is present at the distal end of the exposed portion, and wherein the exposed portion extends from the distal end of the outer sheath; a primary conductor in direct electrical contact with the conforming electrode and adapted to carry ablative energy from an energy source to the conforming electrode; and a spring at the distal end of the outer sheath, wherein the spring enshrouds at least an enshrouded part of the exposed portion of the conforming electrode.

In still another form, the present invention comprises a method of ablating tissue inside a body cavity using a spring-tip, flexible electrode catheter. The method comprising the steps of (1) acquiring a spring-tip, flexible electrode catheter comprising a catheter sheath having a distal end; a flexible electrode extending from the distal end of the catheter sheath; and a spring at the distal end of the catheter sheath, wherein the spring enshrouds at least a portion of the flexible electrode; (2) inserting the spring-tip, flexible electrode catheter into the body cavity; (3) manipulating the spring against the tissue; (4) applying longitudinal force to the spring to compress the spring and bring the flexible electrode adjacent to the tissue; and (5) supplying ablative energy to the flexible electrode to form a lesion in the tissue via coagulation necrosis.

In another form, the present invention comprises a method of diagnosing or treating tissue inside a body cavity containing ambient fluid. The method comprising the steps of (a) axially suspending a flexible electrode within a coil spring at a distal end of a catheter sheath, wherein the coil spring comprises (i) a distal end, and (ii) a plurality of coils, wherein each coil of the plurality of coils is offset from any adjacent coil by a coil separation distance, and wherein the plurality of coils enshroud an exposed portion of the flexible electrode with a distal end of the flexible electrode proximally inset from the distal end of the coil spring; (b) inserting the axially-suspended, flexible electrode into the body cavity; (c) manipulating the distal end of the spring against the tissue; (d) applying an axial load to compress the plurality of coils, reducing the coil separation distances and bringing the flexible electrode adjacent to the tissue; and (e) supplying ablative energy to the flexible electrode to form a lesion in the tissue via coagulation necrosis.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 31 is a fragmentary, isometric view in partial cross section of a tenth embodiment of the spring-tip, brush electrode catheter according to the present invention, having a compressible bellows mounted at the distal end of the catheter sheath.

FIG. 32 is similar to FIG. 31, but depicts a porous compressible bellows.

FIG. 33 is a fragmentary view in partial cross section of the spring-tip, brush electrode catheter depicted in FIG. 31 with the compressible bellows in an uncompressed configuration.

FIG. 34 is a fragmentary view in partial cross section of the spring-tip, brush electrode catheter depicted in FIGS. 31 and 33 with the compressible bellows in a compressed configuration.

DETAILED DESCRIPTION OF THE INVENTION

Figure 1:
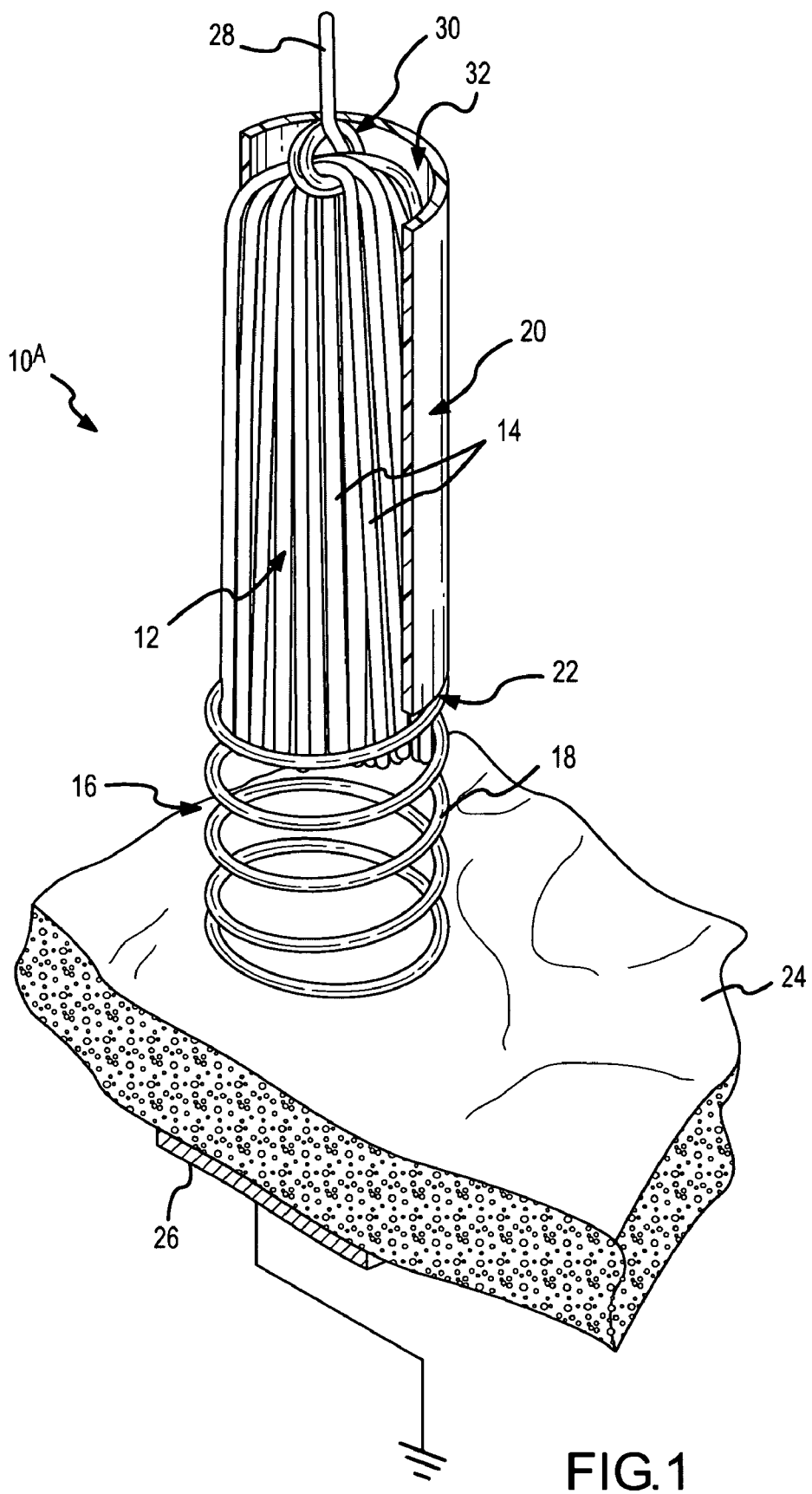
FIG. 1 is fragmentary, isometric view in partial cross section of a first embodiment of a spring-tip, brush electrode catheter for ablation according to the present invention, having a round-wire, coil spring at a distal end of a catheter sheath and shown prior to contact between the brush filaments and the tissue to be ablated.

The present invention comprises a spring-tip, flexible electrode catheter (see, e.g., element $10^4$ in FIGS. 1-5), and a method of using that spring-tip, flexible electrode catheter, to improve the efficacy of flexible-electrode ablation, including radiofrequency ablation. "Flexible electrodes" include, among other things, brush electrodes (see, e.g., element 12 in FIG. 1 and element 74 in FIG. 10), which may comprise a plurality of conductive and/or nonconductive brush filaments (e.g., element 14 in FIG. 1), and rolled electrodes, which may comprise a roll of conductive or nonconductive fabric (not shown). Flexible electrodes may be "dry" electrodes or "wet" electrodes. A wet-brush electrode, for example, is a brush electrode that has conductive or nonconductive fluid delivered to interstitial spaces or gaps between the brush filaments. U.S. utility patent application Ser. No. 10/808,919, which was filed on 24 Mar. 2004 and which is entitled, "Brush Electrode and Method for Ablation" (the '919 application), provides additional details about various dry-brush and wet-brush electrodes. The '919 application is hereby incorporated by reference as though fully set forth herein.

Several embodiments of the spring-tip, flexible electrode catheter according to the present invention are depicted in the figures and described below. To aid in understanding how the spring-tip, flexible electrode catheter of the present invention increases the efficacy of this type of ablation, the flexible electrode is described below as a brush electrode. As noted above, however, a variety of different flexible electrodes could be substituted for the brush electrode that is specifically shown in the drawings and described below.

As described further below, the "spring tip" (e.g., element 16 in FIG. 1) includes a "spring" (e.g., element 18 in FIG. 1) around the flexible electrode (e.g., element 12 in FIG. 1). The "spring" may comprise, among other things, a coil, a mesh, or a bellows. The "spring tip" provides axial suspension, and is capable of axial compression and extension, and is flexible enough for deflection and bending.

With all of the embodiments described herein, the "spring" may be of uniform or varying cross section. Also, depending upon the particular application for the spring-tip, flexible electrode catheter, the spring may be electrically conductive or nonconductive. For instance, when used for epicardial applications, the electrically conductive coil provides a high electric field at the electrode-tissue interface, which helps create fast and deep lesions. On the other hand, when used for endocardial applications, the electrically insulated spring mitigates the electric field leakage along the length of the electrode and, consequently, reduces coagulum formation on the surface of the electrode.

Finally, it should be noted that, for simplicity, the catheter sheath 20 (see, e.g., FIG. 1) is shown in all of the embodiments as having a circular cross section. The catheter sheath could, however, have other than a circular cross section.

Round-Wire, Coil Spring, Flexible Electrode Catheter [1st-3rd Embodiments]

FIGS. 1-5 depict a first embodiment $10^4$ of a spring-tip, flexible electrode catheter for tissue ablation according to the present invention. As previously mentioned, the flexible electrode catheter $10^4$ depicted in FIGS. 1-5, as well as the remaining figures of the present application, is a brush electrode 12 comprising a plurality of conductive and/or nonconductive brush filaments 14. Different types of flexible electrodes may be used in a spring-tip, flexible electrode catheter according to the present invention.

In the first embodiment of the present invention, the spring-tip, brush electrode catheter $10^4$ comprises a round-wire, coil spring 18 at a distal end 22 of the catheter sheath 20. As clearly shown in FIG. 1, the brush filaments 14 are enshrouded by the round-wire, coil spring 18 that, in this embodiment, extends away from the distal end 22 of the catheter sheath 20. The tissue 24 being ablated is shown schematically, as is a grounding pad or dispersion electrode 26. In the embodiment of FIG. 1, a conductor 28 is looped or noosed around the brush filaments 14 at a connection point 30 inside the catheter lumen 32. In this manner, ablative energy 34 (FIGS. 47-49) is transferred to the flexible electrode 12 (i.e., the brush electrode). Other techniques and structures for transferring the ablative energy from the conductor to the flexible electrode are described in the '919 application, which has been incorporated by reference as though fully set forth herein.

The round-wire, coil spring 18 has a proximal end 36 and a distal end 38. The proximal end 36 of the round-wire, coil spring 18 is affixed to the distal end 22 of the catheter sheath 20. The round-wire, coil spring may be, for example, adhered to the distal end of the outer sheath, or the proximal end of the coil spring may be embedded into the sheath material itself at the distal end 22 of the catheter sheath 20. The round-wire, coil spring helps to contain the brush filaments 14 comprising the brush electrode 12; the coil spring provides mechanical flexibility; and, if conductive or nonconductive fluid is being carried in the lumen 32 of the catheter sheath, the coil spring also provides for some fluid containment.

The round-wire, coil spring 18 is capable of being axially compressed or extended, and it may be deflected or bent. The cross-sectional configuration of the actual round-wire comprising the coil spring may be uniform, or the cross-sectional configuration may vary along the helical longitudinal axis of the round-wire. Further, the coil spring 18 may be electrically conductive or nonconductive depending upon the desired electrical properties for the resulting electrode.

Figure 2:
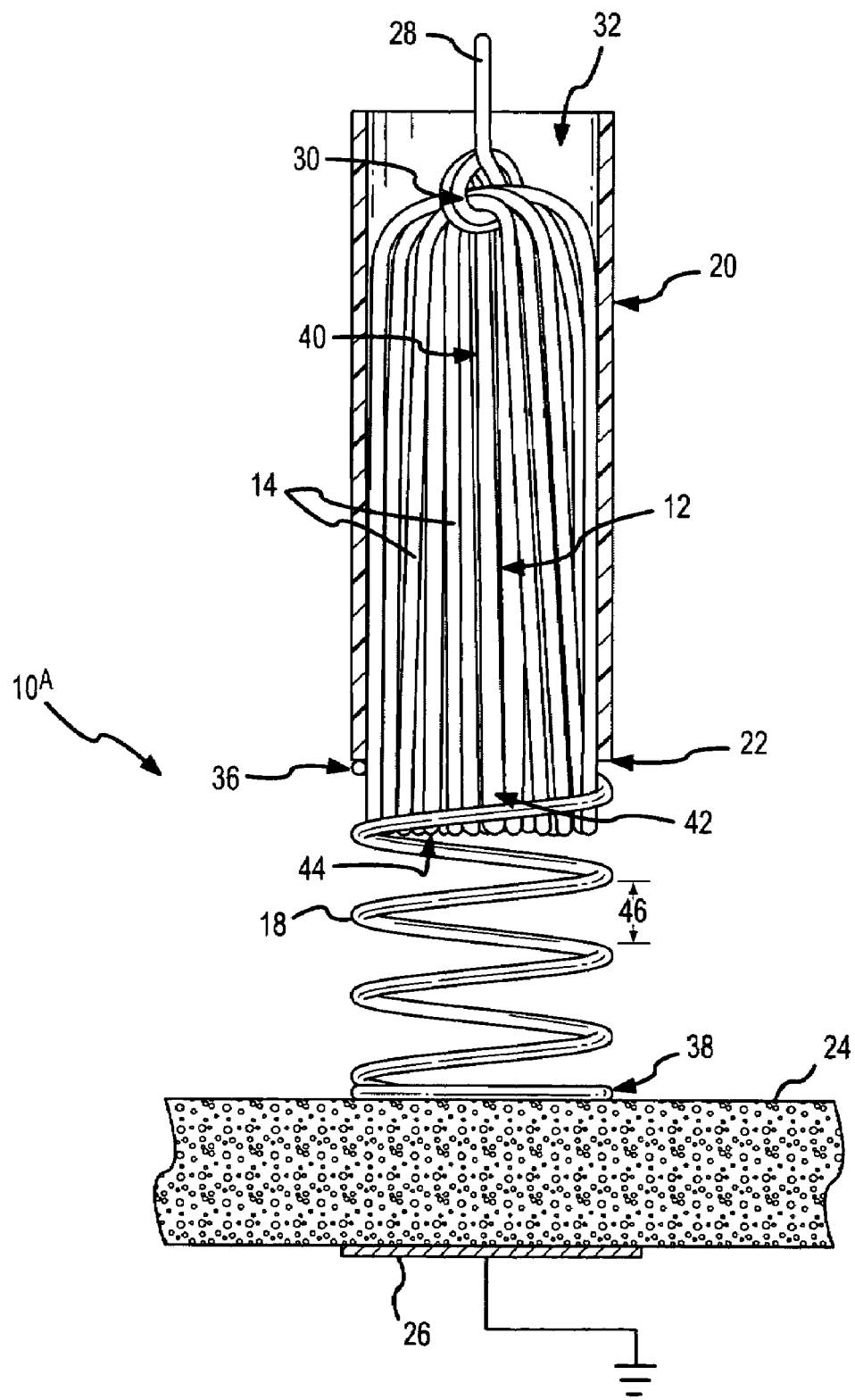
FIG. 2 is a fragmentary view in partial cross section of the spring-tip, brush electrode catheter depicted in FIG. 1 with the round-wire, coil spring in an uncompressed configuration.

FIG. 2 is a fragmentary view in partial cross section of the spring-tip brush electrode catheter $10^4$ depicted in FIG. 1. In this view, the round-wire, coil spring 18 is substantially uncompressed. The brush electrode 12 includes an embedded portion 40 and an exposed portion 42. The embedded portion 40 is contained in the lumen 32, within the outer catheter sheath 20, and does not project from the distal end 22 of the outer catheter sheath. The exposed portion 42, on the other hand, is that portion of the brush electrode 12 which extends distally from the distal end 22 of the outer sheath 20. At the extreme distal end of the brush electrode is a working surface 44 that is adapted to supply the ablative energy 34 to the tissue 24 being ablated. As depicted in FIG.

2, the distal end 38 of the round-wire, coil spring, may be placed against the tissue to be ablated. The individual coils of the round-wire, coil spring are spaced from each other by a coil separation distance 46.

Figure 3:
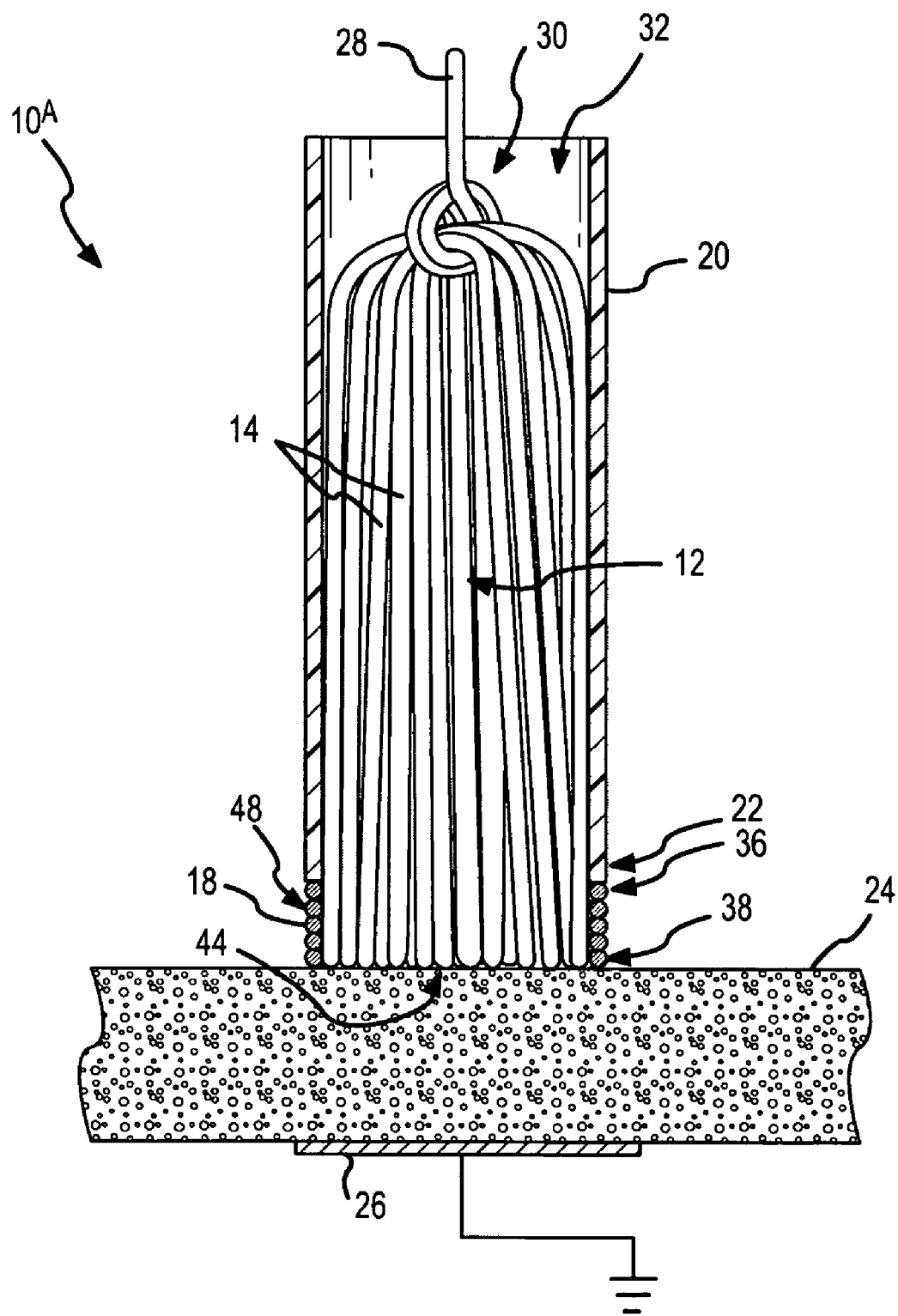
FIG. 3 is similar to FIG. 2, but depicts the spring-tip, brush electrode catheter of FIGS. 1 and 2 with the round-wire, coil spring under compression and the brush filaments in contact with the tissue to be ablated.

FIG. 3 is similar to FIG. 2, but depicts the spring-tip, brush electrode catheter $10^A$ of FIGS. 1 and 2 with the round-wire, coil spring 18 under compression. When the round-wire, coil spring is thus compressed, the working surface 44 of the brush electrode 12 is brought adjacent to, or into contact with, the tissue 24. If desired, the exposed portion 42 of the brush electrode 12 may be configured so that the distal ends of the brush filaments 14, which together comprise the working surface 44, extend slightly passed the distal end 38 of the round-wire, coil spring 18 when the coils are fully compressed (i.e., when the coil separation distance 46 is zero and the coils are stacked one upon the other creating a cylindrical shield 48 around the brush electrode 12). As suggested above, it may also be desirable to configure the brush filaments 14 so that they cannot reach the tissue 24, even when the coils are stacked as depicted in FIG. 3 (see, e.g., FIG. 41, which is discussed further below).

Figure 4:
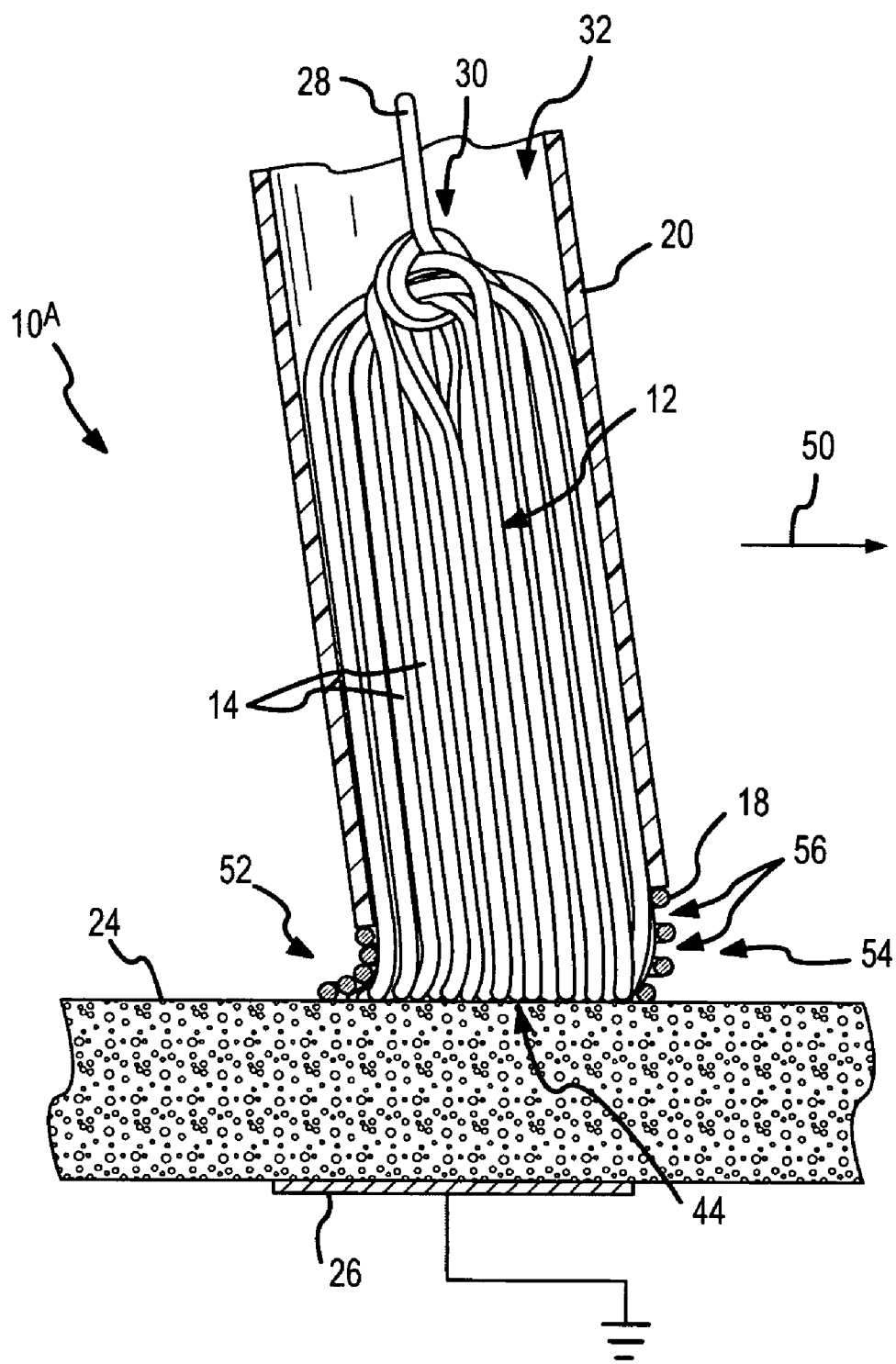
FIG. 4 is similar to FIG. 3, but depicts the spring-tip, brush electrode catheter of FIGS. 1-3 in motion across the tissue that is being ablated, with the catheter sheath leaning away from the direction of travel.

FIG. 4 is similar to FIG. 3, but depicts the spring-tip, brush electrode catheter $10^A$ of FIGS. 1-3 in motion across the tissue 24 that is being ablated. If, for example, the spring-tip, flexible electrode catheter $10^A$ is being used to form a linear lesion on the tissue, the electrode may be moved in the direction of arrow 50 while the ablative energy 34 (see, e.g., FIG. 47) is delivered by the conductor 28 to the brush electrode 12. In FIG. 4, the catheter sheath 20 of the spring-tip, brush electrode catheter $10^A$ is leaning away from the direction of travel 50. In other words, the spring-tip, brush electrode catheter $10^A$ as depicted in FIG. 4 is being pushed across the surface of the tissue being ablated.

While the spring-tip, brush electrode catheter $10^A$ is in motion as shown in FIG. 4, the stacked coils of the round-wire, coil spring define a trailing surface 52 and a leading surface 54. As depicted in FIG. 4, the stacked coils forming the trailing surface 52 may ride one on top of the other, creating a relatively solid surface and thereby inhibiting the ability of any fluid that may be flowing axially in the lumen 32 of the outer sheath from leaking through the trailing surface 52. The coils forming the leading surface 54, on the other hand, are not necessarily stacked directly on top of each other and may define a series of spaced gaps 56 that permit the conductive or nonconductive fluid to exit ahead of the spring-tip, brush electrode catheter $10^A$. This forward-exiting, conductive or nonconductive fluid may impinge upon the tissue 24 being ablated just prior to when the brush electrode 12 itself travels over that tissue during the ablation procedure. The tissue 24 may be, thereby, cooled slightly before ablative energy is delivered to the tissue, which can help avoid undesirable charring of the tissue. Since the cylindrical shield 48 (see FIG. 3) of stacked spring coils inhibits contact between the surrounding blood and the brush electrode 12, the formation of undesirable coagulum is also reduced.

Figure 5:
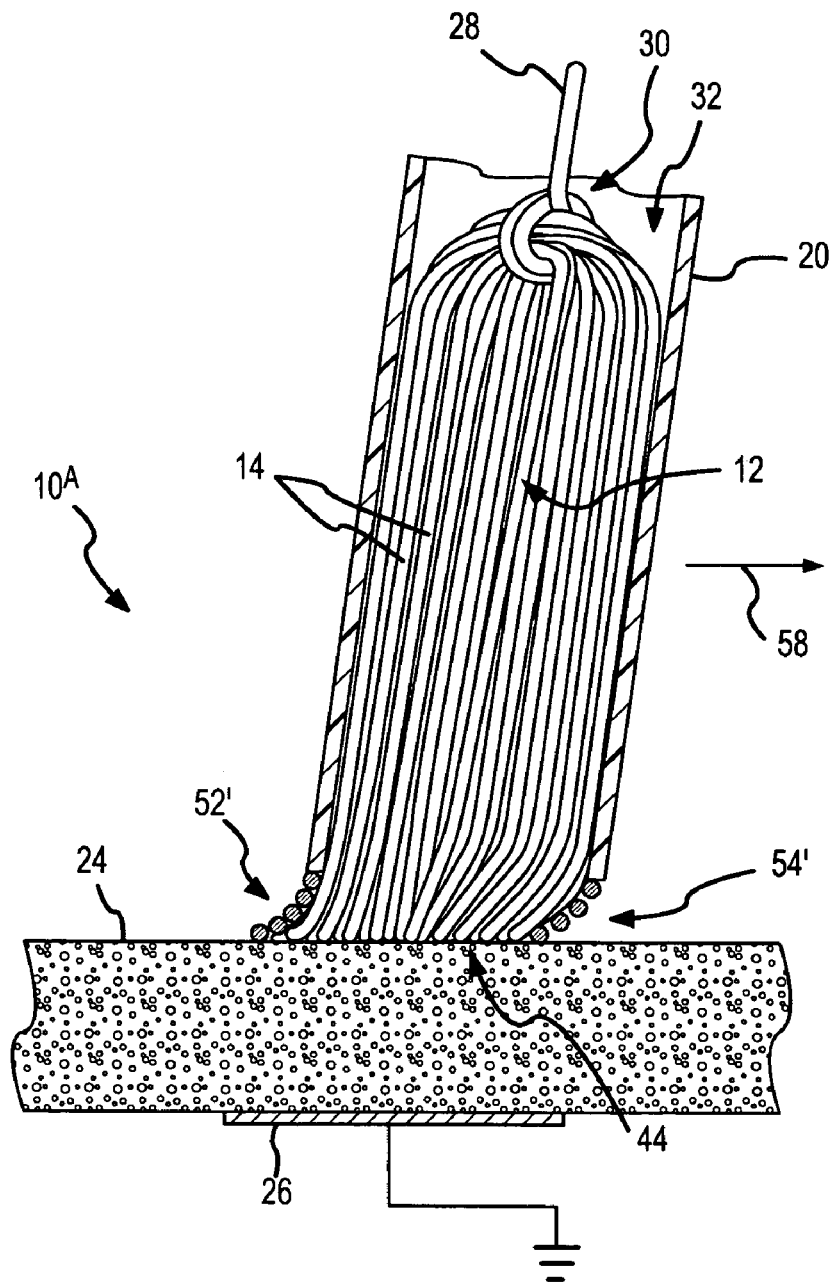
FIG. 5 is similar to FIG. 4, but depicts the spring-tip, brush electrode catheter of FIGS. 1-3 in motion across the tissue that is being ablated, with the catheter sheath leaning toward the direction of travel.

FIG. 5 is similar to FIG. 4, but depicts the spring-tip, brush electrode catheter $10^A$ in motion across the tissue 24 with the catheter sheath 20 leaning toward the direction of travel 58. In other words, as depicted in FIG. 5, the spring-tip, flexible electrode catheter $10^A$ is being more or less dragged across the tissue 24 that is being ablated, rather than pushed across the tissue as it was in FIG. 4. Again, the stacked coils form a cylindrical shield that has a trailing surface 52' and a leading surface 54'. As described in connection with FIG. 4, the trailing surface 52' is preferably less "leaky" than the leading surface 54'. If there are no gaps between the coils defining the trailing surface 52' of the cylindrical shield, the blood is inhibited from reaching the brush electrode 12 through the trailing surface, which can help prevent the formation of undesirable coagulum. Also, similar to what was discussed in connection with FIG. 4, the "leaky" leading surface 54' permits any conductive or non-conductive fluid traveling within the lumen 32 of the outer sheath 20 to impinge upon the tissue 24 that is about to be ablated just prior to when the working surface 44 of the brush electrode is dragged across the tissue during the formation of a linear lesion.

Figure 6:
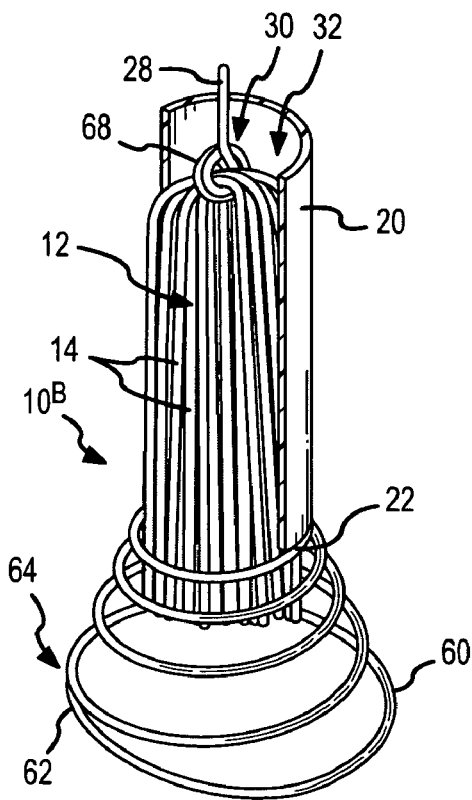
FIG. 6 is a fragmentary, isometric view in partial cross section of a second embodiment of the spring-tip, brush electrode catheter according the present invention, having an outwardly-tapering, round-wire, coil spring at the distal end of the catheter sheath.

FIGS. 6-9 depict a second embodiment $10^B$ of the spring-tip, flexible electrode catheter of the present invention. In this embodiment, the flexible electrode is again depicted as a brush electrode 12, similar to what is shown in FIGS. 1-5. FIG. 6 is a fragmentary, isometric view in partial cross section of the second embodiment $10^B$ and clearly shows that the round-wire, coil spring 18 depicted in FIGS. 1-5 has been replaced with an outwardly-tapering, round-wire, coil spring 60. As with the round-wire, coil spring 18 depicted in FIGS. 1-5, the outwardly-tapering, coil spring 60 depicted in FIGS. 6-9 is configured so that the coil spring does not have a free or detached longitudinal end at the distal end of the spring. As depicted in FIG. 6, the longitudinal end 62 of the coil spring 60 has been affixed to or "blended into" the coil spring itself at a connection point 64.

Figure 7:
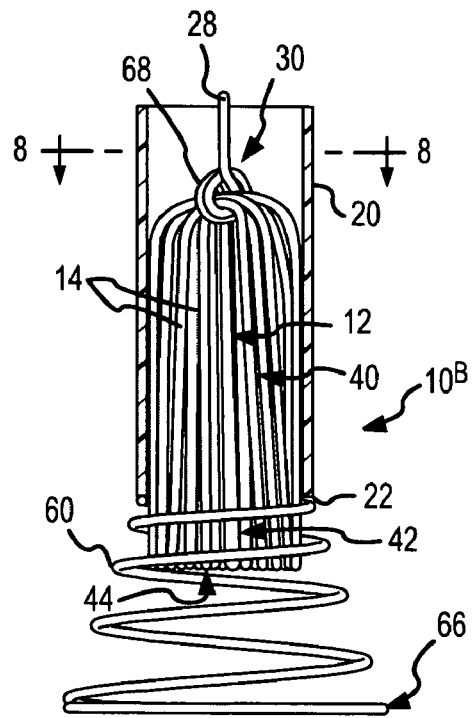
FIG. 7 is a fragmentary view in partial cross section of the spring-tip, brush electrode catheter depicted in FIG. 6 prior to compression of the outwardly-tapering, round-wire, coil spring.

FIG. 7 is a fragmentary view in partial cross section of the spring-tip, brush electrode catheter $10^B$ depicted in FIG. 6 and is most similar to FIG. 2 of the first embodiment. As shown in FIG. 7, the outwardly-tapering, round-wire, coil spring 60 is uncompressed. In this configuration, the working surface 44 at the distal end of the brush electrode 12 is recessed inside the coil spring 60, away from the distal end 66 of the outwardly-tapering, round-wire, coil spring.

Figure 8:
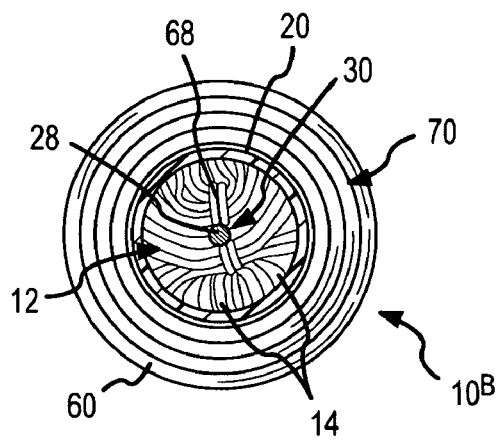
FIG. 8 is a fragmentary view in partial cross section taken along line 8-8 of FIG. 7 and depicting the slightly overlapping configuration of the coils comprising the outwardly-tapering, round-wire, coil spring.

FIG. 8 is a fragmentary view in partial cross section taken along line 8-8 of FIG. 7. In FIG. 8, the bundle of filaments comprising the brush electrode 12 may be clearly seen. The conductor 28 that delivers the ablative energy to the bundle of filaments is shown in cross section, and a loop or noose 68 of uninsulated conductor is also shown around the bundle of filaments 14. In order to ensure that the outwardly-tapering, round-wire, coil spring 60 is adapted to provide a shield 70 (see also FIG. 9) around the brush filaments 14 during ablation, the coils of the spring 60 are oriented in a slightly overlapping configuration that is clearly visible in FIG. 8. In particular, as shown in this figure, each coil of the outwardly-tapering, round-wire, coil spring 60 is arranged to overlap slightly with any adjacent spring coils.

Figure 9:
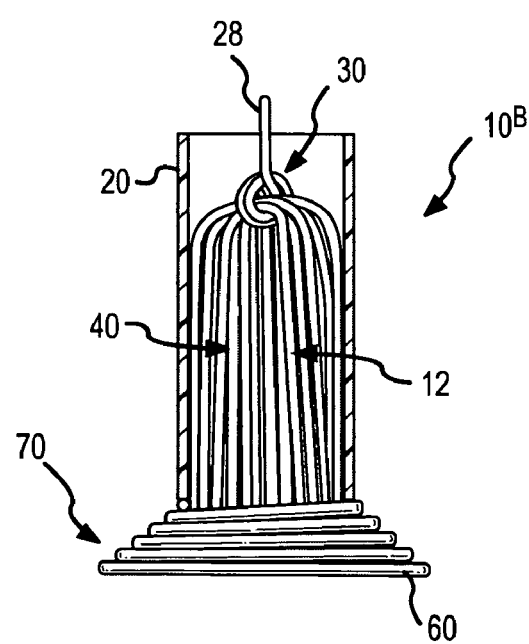
FIG. 9 is a fragmentary view in partial cross section of the spring-tip, brush electrode catheter depicted in FIGS. 6-8 with the outwardly-tapering, round-wire, coil spring under compression.

FIG. 9 is a fragmentary view in partial cross section of the spring-tip, brush electrode catheter depicted $10^B$ in FIGS. 6-8. In the configuration depicted in FIG. 9, the outwardly-tapering, round-wire, coil spring 60 has been compressed to bring the working surface 44 of the brush electrode 12 closely adjacent to, or into contact with, the tissue to be ablated. As shown in FIG. 9, the compressed coil spring forms an expanding, frustal-conical shield 70 of stair-stepped, spring coils around the exposed portion 42 (not visible in FIG. 9) of the brush electrode.

Although not depicted in the figures, the embodiment of the spring-tip, flexible electrode catheter depicted in FIGS. 6-9 may be pushed or dragged across the tissue to form a linear lesion as described in connection with the first embodiment in FIGS. 4 and 5. Again, the stacked coils help to shield the flexible electrode (e.g., the brush electrode 12) from the surrounding blood, and permit leakage of any conductive or nonconductive fluid that may be flowing through the lumen 32 of the catheter sheath 20 toward the distal end 22 of the catheter sheath 20 so as to impinge upon the tissue to be ablated just prior to the actual ablation taking place. This ability to push or drag the spring-tip, flexible catheter along tissue being ablated to form a linear lesion holds true for all of the above and below described embodiments.

Figure 10:
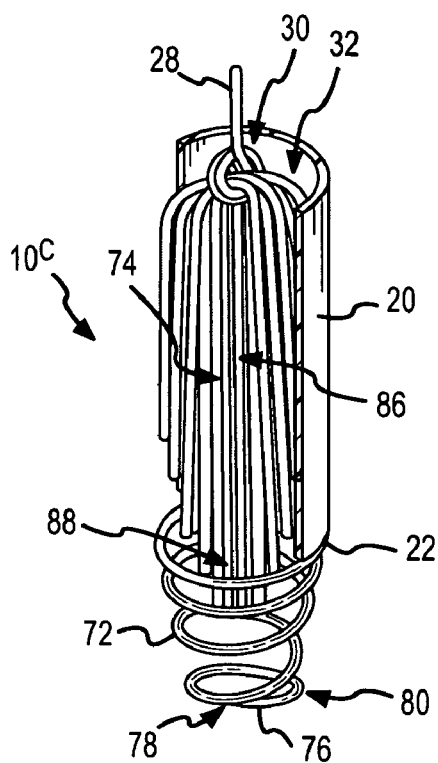
FIG. 10 is a fragmentary, isometric view in partial cross section of a third embodiment of the spring-tip, brush electrode catheter according to the present invention, having an inwardly-tapering, round-wire, coil spring at the distal end of the catheter sheath.
Figure 11:
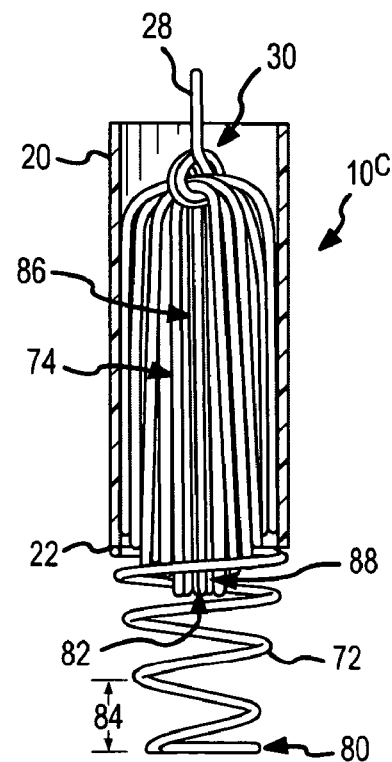
FIG. 11 is a fragmentary view in partial cross section of the spring-tip, brush electrode catheter depicted in FIG. 10 prior to compression of the inwardly-tapering, round-wire, coil spring.
Figure 12:
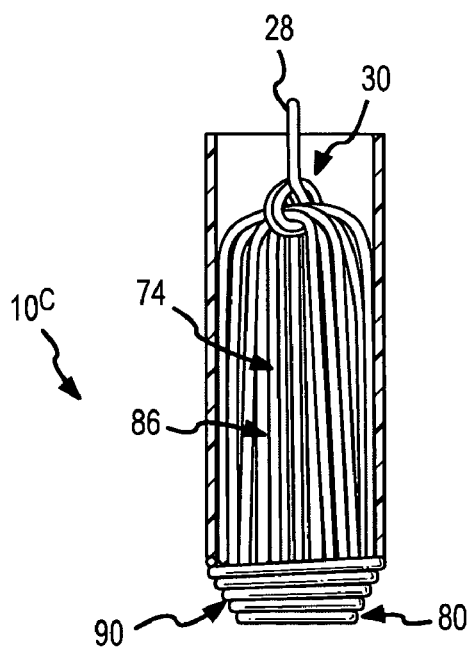
FIG. 12 is a fragmentary view in partial cross section of the spring-tip, brush electrode catheter depicted in FIGS. 10 and 11 with the inwardly-tapering, round-wire, coil spring under compression.

FIGS. 10-12 depict a third embodiment $10^C$ of the spring-tip, flexible electrode catheter according to the present invention. This embodiment comprises an inwardly-tapering, round-wire, coil spring 72 at the distal end 22 of the catheter sheath 20. FIG. 10 is a fragmentary, isometric view in partial cross section. A tapered brush electrode 74 is connected to the conductor 28 in this embodiment. The distal, longitudinal end 76 of the round-wire, coil spring 72 is, again, "blended into" one of the coils at a connection point 78 to create a relatively smooth contact surface at the distal end 80 of the inwardly-tapering, round-wire coil spring 72.

FIG. 11 is a fragmentary view in partial cross section of the spring-tip, brush electrode catheter $10^C$ depicted in FIG. 10 prior to compression of the coil spring 72. This figure also clearly shows that the brush electrode 74 may be tapered slightly to better fit within the interior of the inwardly-tapering, round-wire, coil spring 72 once the coil spring has been compressed, bringing a distal tip 82 of the tapered brush electrode 74 adjacent to the distal end 80 of the coil spring 72. In its uncompressed configuration depicted in FIG. 11, the coil spring 72 comprises a plurality of coils separated by a coil separation distance 84. As also clearly shown in FIG. 11, the tapered brush electrode 74 comprises an embedded portion 86 and an exposed portion 88.

FIG. 12 is a fragmentary view in partial cross section of the spring-tip, brush electrode catheter $10^C$ depicted in FIGS. 10 and 11 with the inwardly-tapering, round-wire, coil spring 72 under compression. In this configuration, the spring coils are stacked upon each other, thereby forming an inwardly-tapering, frustal-conical shield 90 of spring coils around the exposed portion 88 (not visible in FIG. 12) of the brush electrode 74. In this configuration, the distal tip 82 (FIG. 11) of the tapered brush electrode 74 is closely adjacent to the tissue (not shown in FIGS. 10-12 for simplicity) being ablated.

Flat-Wire, Coil Spring, Flexible Electrode Catheter [4th-6th Embodiments]

Figure 13:
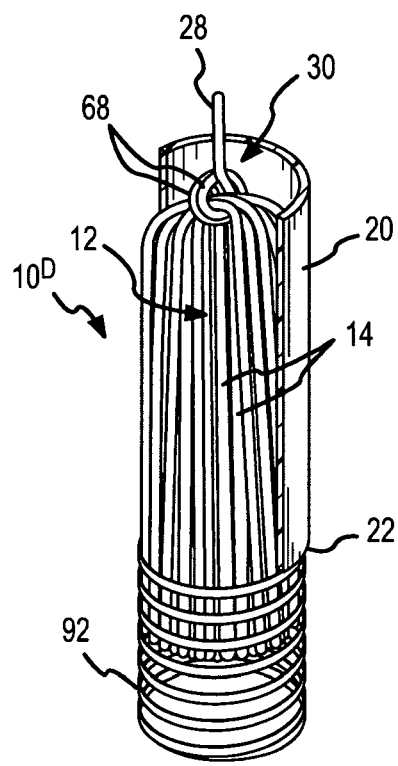
FIG. 13 is a fragmentary, isometric view in partial cross section of a fourth embodiment of the spring-tip, brush electrode catheter according to the present invention, having a flat-wire, coil spring at the distal end of the catheter sheath.
Figure 14:
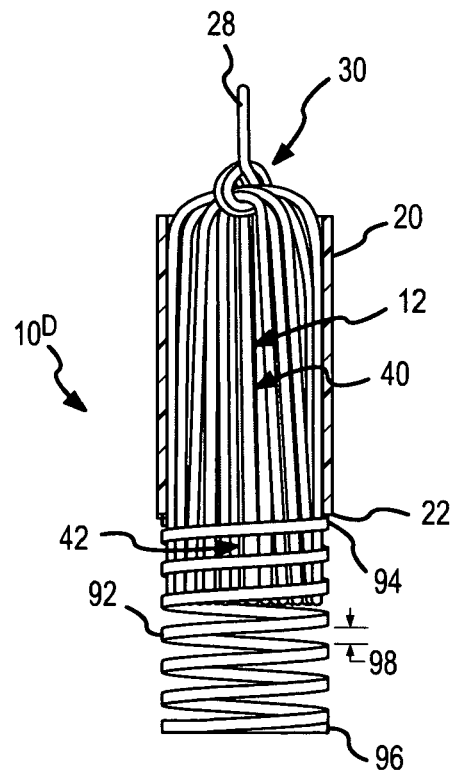
FIG. 14 is a fragmentary view in partial cross section of the spring-tip, brush electrode catheter depicted in FIG. 13 prior to compression of the flat-wire, coil spring.
Figure 15:
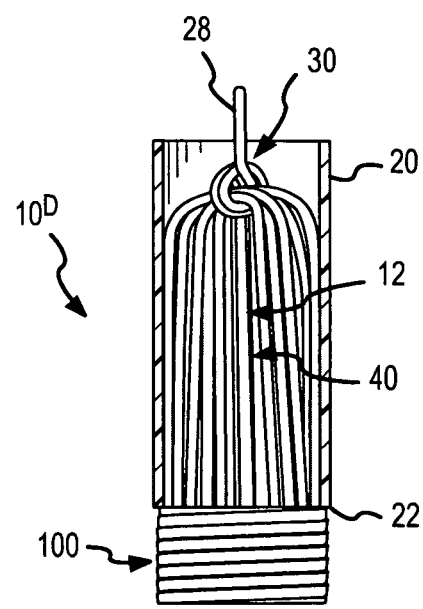
FIG. 15 is a fragmentary view in partial cross section of the spring-tip, brush electrode catheter depicted in FIGS. 13 and 14 with the flat-wire, coil spring under compression.

FIGS. 13-15 depict a fourth embodiment $10^D$ of the spring-tip, flexible electrode catheter according to the present invention. This embodiment is similar to the embodiment depicted in FIGS. 1-5; however, the coil spring depicted in FIGS. 13-15 is a flat-wire, coil spring 92 rather than a round-wire, coil spring 18.

FIG. 13 is a fragmentary, isometric view in partial cross section of this embodiment of the spring-tip, brush electrode catheter $10^D$. Again, the conductor 28 delivers ablative energy 34 (see, e.g., FIG. 47) to the brush electrode 12 at a connection point 30. As shown in FIGS. 13-15, the connection point 30 may be one or more loops or nooses 68 of uninsulated conductor wrapped around a portion of the brush filaments 14. For all of the embodiments disclosed herein, the conductor may deliver ablative energy to the flexible electrode by means that are different from what is shown in the figures. As previously mentioned, other techniques and structures for transferring the ablative energy from the conductor to the flexible electrode are described in the '919 application, which has been incorporated by reference as though fully set forth herein.

FIG. 14 is a fragmentary view in partial cross section of the spring-tip, brush electrode catheter $10^D$ depicted in FIG. 13 prior to compression of the flat-wire, coil spring 92. The coil spring includes a proximal end 94 affixed at the distal end 22 of the outer catheter sheath 20. The coil spring 92 also comprises a distal end 96 that is displaced from the distal end 22 of the outer catheter sheath 20. In this uncompressed configuration, the flat-wire, coil spring 92 comprises a plurality of coils that are offset from any adjacent coils by a coil separation distance 98. Although the coil separation distance 98 is shown in each of the drawing as remaining substantially constant along the spring, the separation distance for any of the embodiments disclosed herein may vary along the length of the spring. The brush electrode 12 again comprises an embedded portion 40 and an exposed portion 42. As the flat-wire, coil spring 92 is compressed, the exposed portion 42 of the brush electrode moves toward the distal end 96 of the coil spring 92 and, thus, closer to the tissue to be ablated.

FIG. 15 is a fragmentary view in partial cross section of the spring-tip, brush electrode catheter $10^D$ depicted in FIGS. 13 and 14. In this figure, however, the flat-wire, coil spring 92 has been fully compressed. In this fully-compressed configuration, the spring coils form a cylindrical shield 100 around the exposed portion 42 (not visible in FIG. 15) of the brush electrode 12. The coils of the flat-wire, coil spring 92 thus function in a manner that is similar to the manner in which the coils of the previous embodiments function.

Figure 16:
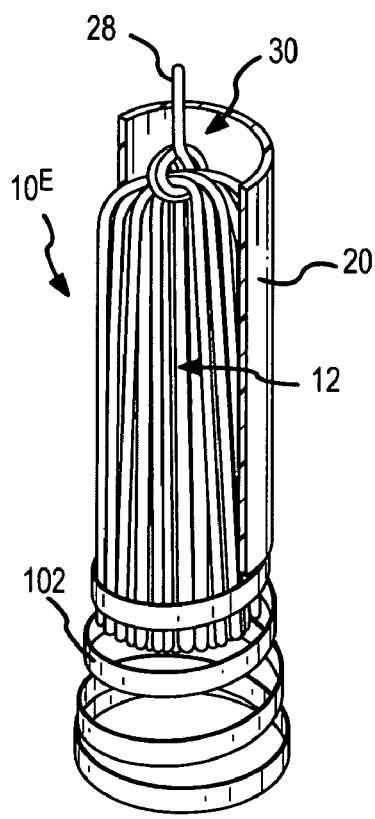
FIG. 16 is a fragmentary, isometric view in partial cross section of a fifth embodiment of the spring-tip, brush electrode catheter according the present invention, having an outwardly-tapering, flat-wire, coil spring at the distal end of the catheter sheath.
Figure 17:
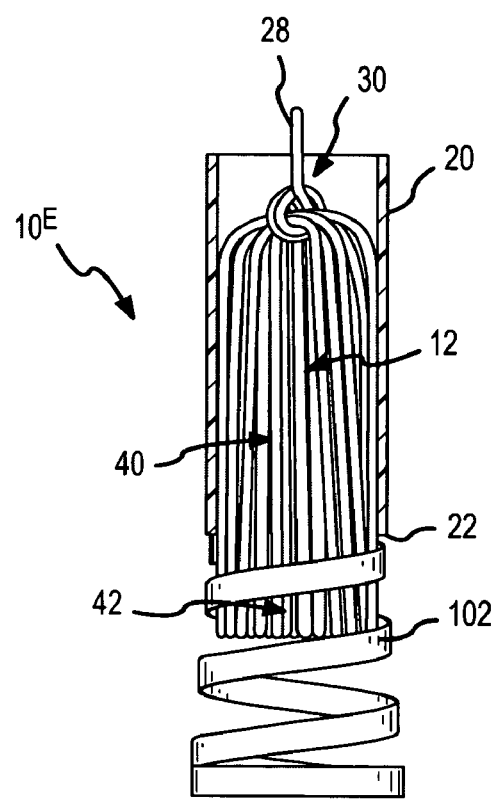
FIG. 17 is a fragmentary view in partial cross section of the spring-tip, brush electrode catheter depicted in FIG. 16 prior to compression of the outwardly-tapering, flat-wire, coil spring.
Figure 18:
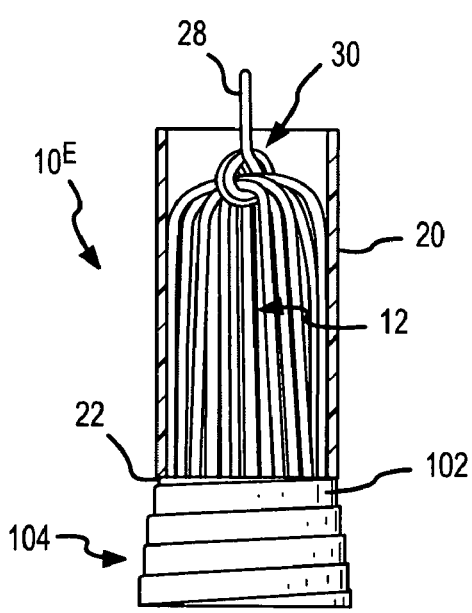
FIG. 18 is a fragmentary view in partial cross section of the spring-tip, brush electrode catheter depicted in FIGS. 16 and 17 with the outwardly-tapering, flat-wire, coil spring under compression.

FIGS. 16-18 depict a fifth embodiment of the spring-tip, brush electrode catheter $10^E$ according to the present invention. As shown in FIG. 16, which is a fragmentary, isometric view in partial cross section, this embodiment comprises an outwardly-tapering, flat-wire, coil spring 102 at the distal end 22 of the catheter sheath 20. FIG. 17 is a fragmentary view in partial cross section of the spring-tip, brush electrode catheter $10^E$ depicted in FIG. 16 prior to compression of the coil spring 102. FIG. 18 depicts the spring-tip, brush electrode catheter of FIGS. 16 and 17 with the outwardly-tapering, flat-wire, coil spring 102 under compression. As shown to good advantage in this latter figure, when the flat-wire, coil spring 102 is compressed, the coils form an expanding, frustal-conical shield 104 of spring coils around the exposed portion 42 (not visible in FIG. 18) of the brush electrode. Again, the spring-tip, flexible electrode catheter $10^E$ depicted in FIGS. 16-18 may be used to create spot lesions or linear lesions as previously described in connection with the above embodiments.

Figure 19:
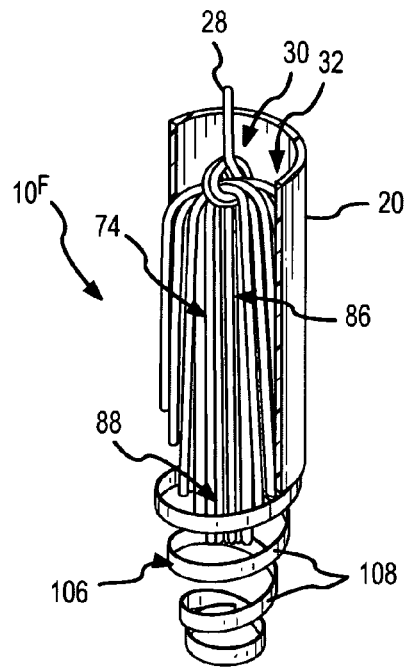
FIG. 19 is a fragmentary, isometric view in partial cross section of a sixth embodiment of the spring-tip, brush electrode catheter according to the present invention, having an inwardly-tapering, flat-wire, coil spring at the distal end of the catheter sheath.
Figure 20:
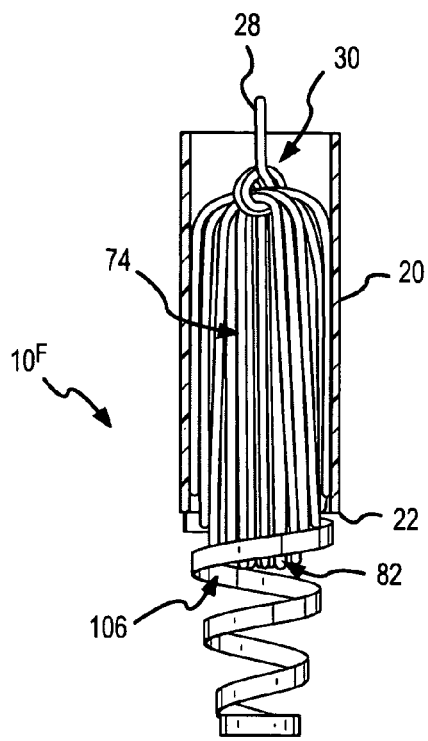
FIG. 20 is a fragmentary view in partial cross section of the spring-tip, brush electrode catheter depicted in FIG. 19 prior to compression of the inwardly-tapering, flat-wire, coil spring.
Figure 21:
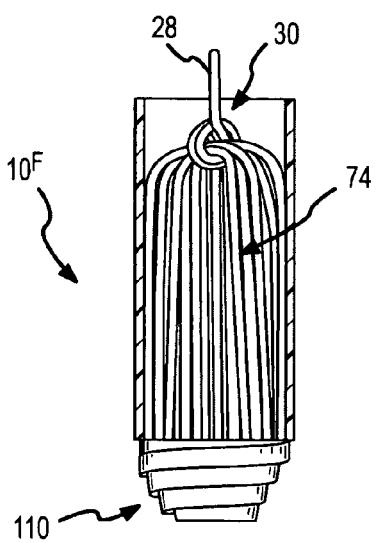
FIG. 21 is a fragmentary view in partial cross section of the spring-tip, brush electrode catheter depicted in FIGS. 19 and 20 with the inwardly-tapering, flat-wire, coil spring under compression.

FIGS. 19-21 depict a sixth embodiment $10^F$ of the spring-tip, brush electrode catheter according to the present invention. In this embodiment, the coil spring is a inwardly-tapering, flat-wire, coil spring 106 that includes a plurality of concentric coils 108. As discussed in connection with the third embodiment (i.e., FIGS. 10-12), the flexible electrode used with the inwardly-tapering, flat-wire coil spring may be a tapered brush electrode 74 as shown in FIGS. 19-21. The tapered brush electrode depicted in FIGS. 19-21 includes a distal tip 82 that is configured to fit within the smallest coil of the inwardly-tapering, flat-wire coil spring (i.e., the last coil, adjacent to the distal end of the coil spring).

FIG. 20 is a fragmentary view in partial cross section of the spring-tip, brush electrode catheter $10^F$ depicted in FIG. 19 prior to compression of the inwardly-tapering, flat-wire, coil spring 106. FIG. 21 is a fragmentary view in partial cross section of the spring-tip, brush electrode catheter depicted in FIGS. 19 and 20. In FIG. 21, however, the inwardly-tapering, flat-wire, coil spring 106 is under compression. In its compressed configuration, the coil spring forms a tapering, frustal-conical shield 110 of spring coils. As discussed above, these coils serve a number of functions in the present invention. For example, they help contain the brush filaments while permitting mechanical flexibility; they help with fluid containment when conductive or nonconductive fluid is flowing within the lumen 32; they help shield the brush filaments from any surrounding blood; and they may permit the conductive or nonconductive fluid, when present, to impinge upon the tissue just prior to ablation to help form deep lesions while minimizing undesirable effects on the tissue surface (e.g., charring).

Compressible Mesh, Flexible Electrode Catheter [7th-9th Embodiments]

Figure 22:
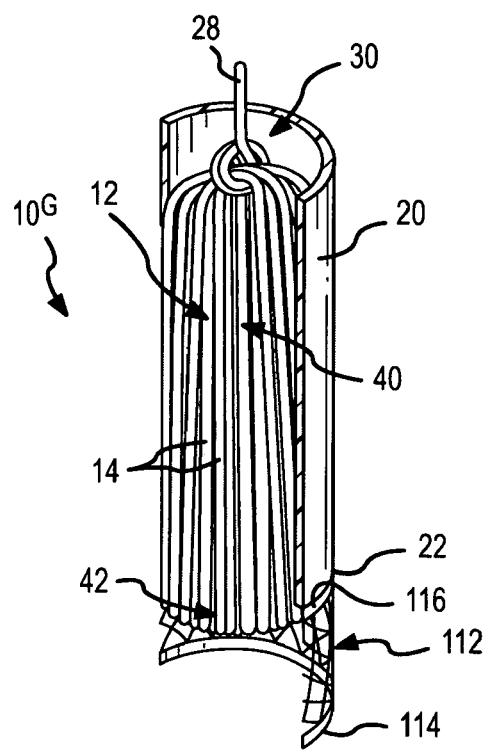
FIG. 22 is a fragmentary, isometric view in partial cross section of a seventh embodiment of the spring-tip, brush electrode catheter according to the present invention, having a compressible mesh at the distal end of the catheter sheath.
Figure 23:
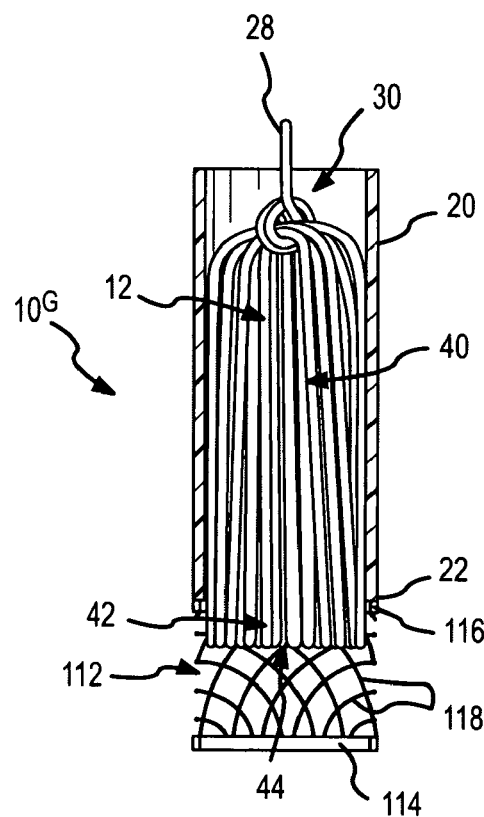
FIG. 23 is a fragmentary view in partial cross section of the spring-tip, brush electrode catheter depicted in FIG. 22 with the compressible mesh in an uncompressed configuration.
Figure 24:
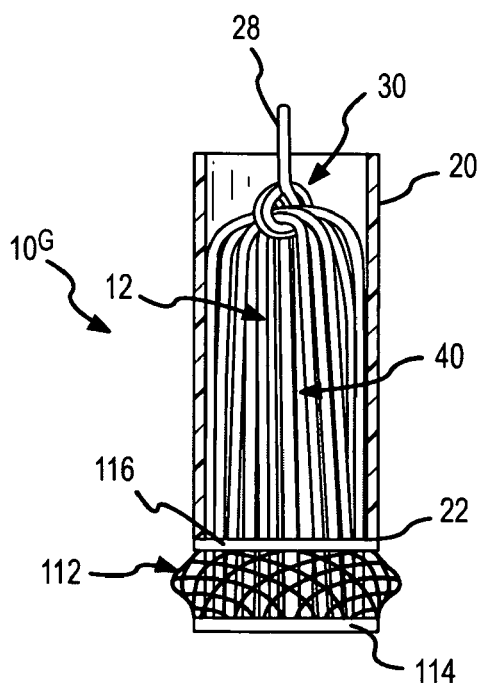
FIG. 24 is a fragmentary view in partial cross section of the spring-tip, brush electrode catheter depicted in FIGS. 22 and 23 with the compressible mesh in a compressed configuration.

FIGS. 22-24 depict a seventh embodiment $10^G$ of the spring-tip, flexible electrode catheter according to the present invention. In this embodiment, the flexible electrode is again depicted as a brush electrode 12. As previously mentioned, different types of flexible electrodes other than brush electrodes could be used. In the configuration depicted in FIGS. 22-24, the conductor 28 is again shown as making electrical contact with the brush electrode 12 via a section of uninsulated conductor looped or noosed around the midsection of the brush filaments 14 before the brush filaments are folded and inserted into the distal end 22 of the outer catheter sheath 20.

FIG. 22 is a fragmentary, isometric view in partial cross section of the spring-tip, brush electrode catheter $10^G$ according to the seventh embodiment of the present invention. In this embodiment, a compressible mesh 112 is present at the distal end 22 of the outer catheter sheath 20. The longitudinal ends or edges of the compressible mesh are contained or embraced by nonconductive or conductive bands. In particular, a distal band 114 is present at one longitudinal edge of the section of compressible mesh 112, and a proximal band 116 is present at the opposite longitudinal edge of the compressible mesh 112.

FIG. 23 is a fragmentary view in partial cross section of the spring-tip, brush electrode catheter $10^G$ depicted in FIG. 22 with the compressible mesh 112 shown in an uncompressed configuration. As clearly shown in this figure, the compressible mesh 112 comprises overlapping and interwoven strands 118 of conductive or nonconductive material. These flexible, overlapping strands 118 form an "open cage" around the exposed portion 42 of the brush electrode 12. Further, as shown in FIG. 24, which is a fragmentary view in partial cross section of the spring-tip, brush electrode catheter depicted in FIGS. 22 and 23 with the compressible mesh in a compressed configuration, the overlapping strands 118 of material are able to flex or bulge outwardly to permit the working surface 44 of the brush electrode to approach the tissue to be ablated. In other words, when the spring-tip, brush electrode catheter $10^G$ is pressed toward the tissue to be ablated, the working surface 44 of the brush electrode 12 moves toward the distal band 114, which would be resting on the tissue that is being ablated. In this embodiment, the compressible mesh 112 again somewhat shields the brush electrode 12 from the surrounding blood. The compressible mesh may, depending upon the precise configuration of the overlapping strands 118, provide a leakier shield than is provided by the previously disclosed shield embodiments (i.e., element 48 in FIG. 3, element 70 in FIGS. 8 and 9, element 90 in FIG. 12, element 100 in FIG. 15, element 104 in FIG. 18, and element 110 in FIG. 21).

Figure 25:
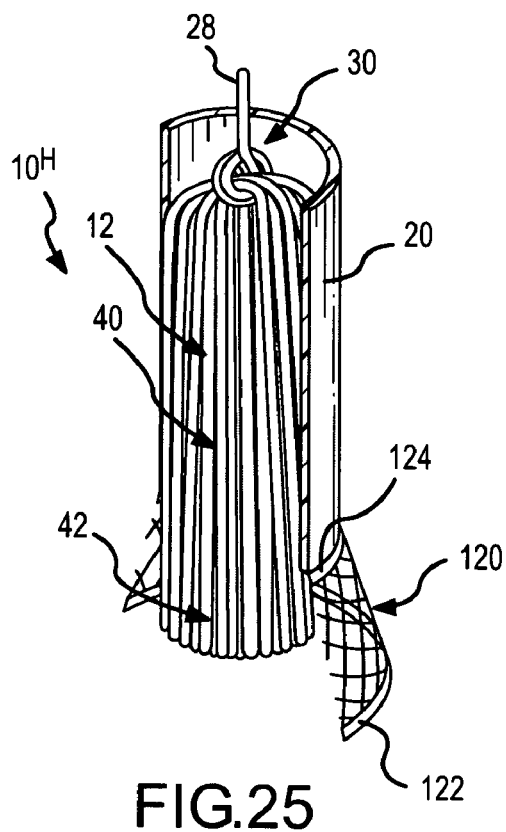
FIG. 25 is a fragmentary, isometric view in partial cross section of an eighth embodiment of the spring-tip, brush electrode catheter according the present invention, having an outwardly-tapering, compressible mesh at the distal end of the catheter sheath.
Figure 26:
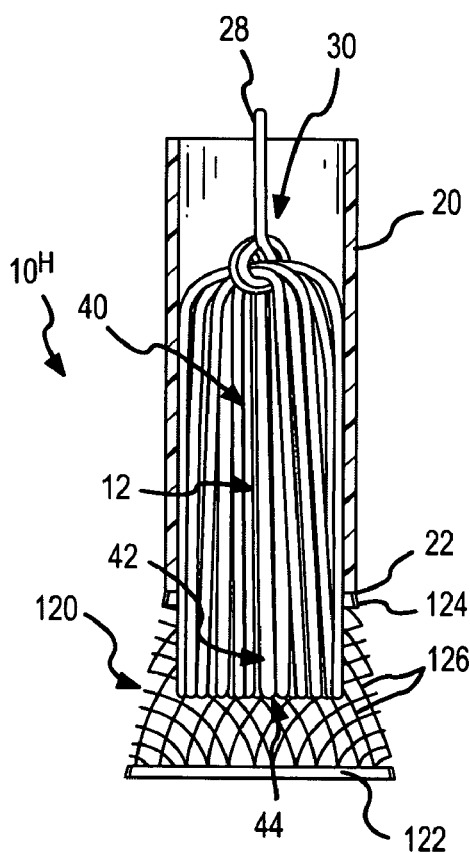
FIG. 26 is a fragmentary view in partial cross section of the spring-tip, brush electrode catheter depicted in FIG. 25 with the outwardly-tapering, compressible mesh in an uncompressed configuration.
Figure 27:
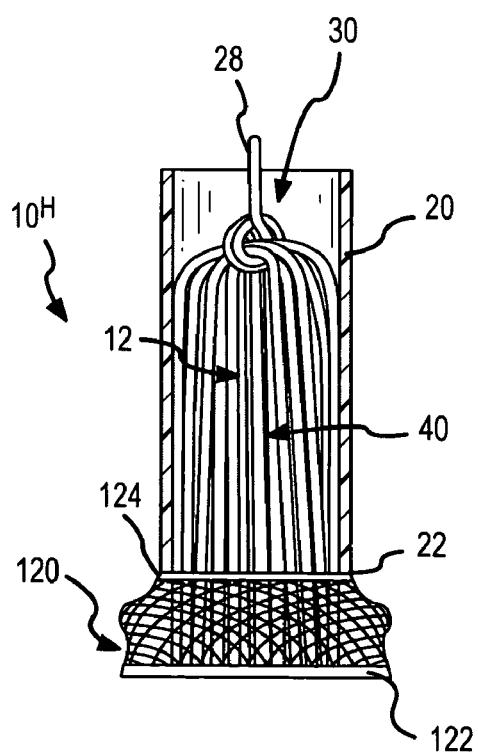
FIG. 27 is a fragmentary view in partial cross section of the spring-tip, brush electrode catheter depicted in FIGS. 25 and 26 with the outwardly-tapering, compressible mesh in a compressed configuration.

FIGS. 25-27 depict an eighth embodiment $10^H$ of the spring-tip, flexible electrode catheter according to the present invention. This embodiment is similar to the embodiment depicted in FIGS. 22-24, but includes an outwardly-tapering, compressible mesh 120 at the distal end 22 of the catheter sheath 20. A distal band 122 in this embodiment is, thus, larger than the proximal band 124. With this configuration, a larger area of tissue is present within the distal band 120 when the distal band is placed against tissue to be ablated than is present with the embodiment depicted in FIGS. 22-24. Thus, the ablative energy, which is at least partially contained and directed by the outwardly-tapering, compressible mesh 120, is delivered to a relatively larger area of tissue.

As shown in FIG. 26, the compressible mesh 120 again comprises overlapping strands 126 of conductive or nonconductive material. When the compressible mesh 120 is compressed to bring the working surface 44 of the brush electrode 12 in proximity to the tissue to be ablated, the compressible mesh 120 may bulge as shown in FIG. 27.

Figure 28:
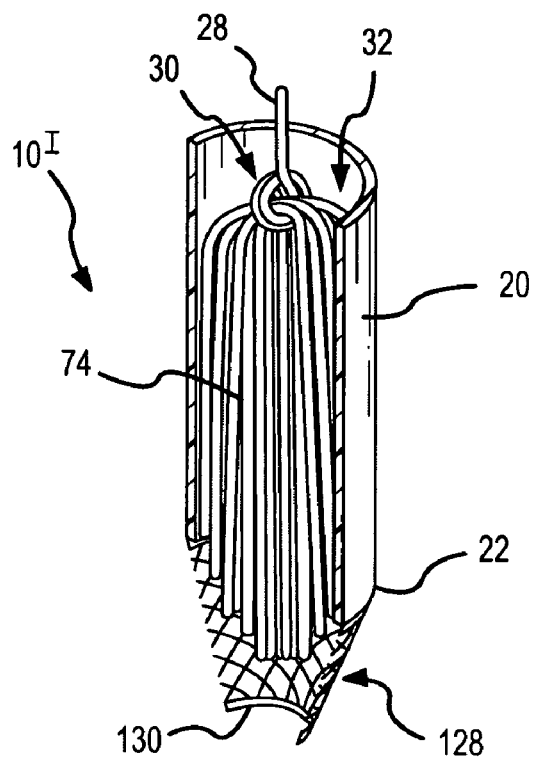
FIG. 28 is a fragmentary, isometric view in partial cross section of a ninth embodiment of the spring-tip, brush electrode catheter according to the present invention, having an inwardly-tapering, compressible mesh at the distal end of the catheter sheath.
Figure 29:
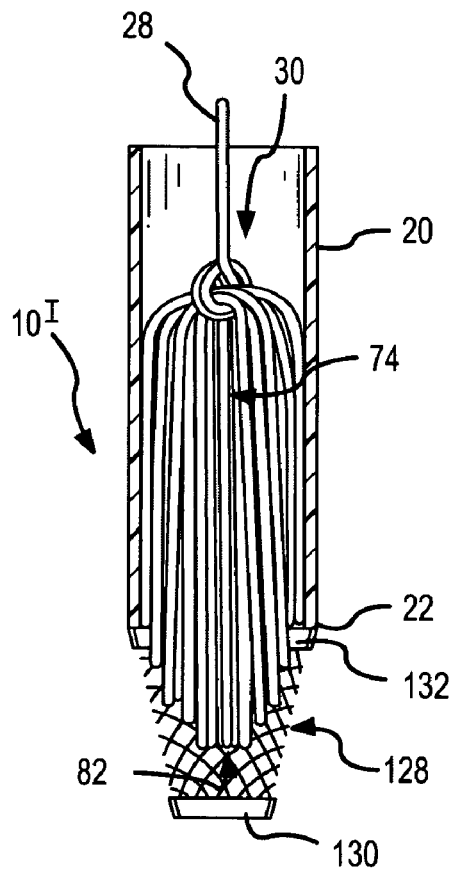
FIG. 29 is a fragmentary view in partial cross section of the spring-tip, brush electrode catheter depicted in FIG. 28 with the inwardly-tapering, compressible mesh in an uncompressed configuration.
Figure 30:
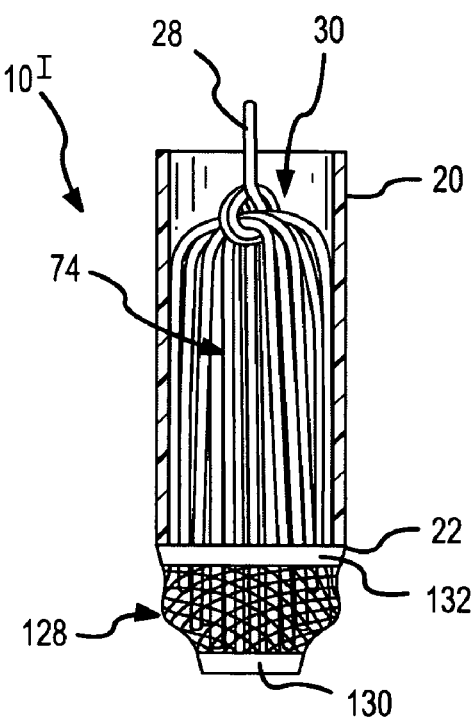
FIG. 30 is a fragmentary view in partial cross section of the spring-tip, brush electrode catheter depicted in FIGS. 28 and 29 with the inwardly-tapering, compressible mesh in a compressed configuration.

FIGS. 28-30 depict a ninth embodiment $10^I$ of the spring-tip, flexible electrode catheter according to the present invention. In this embodiment $10^I$, an inwardly-tapering, compressible mesh 128 is present at the distal end 22 of the outer catheter sheath 20. A distal band 130 and a proximal band 132 are again present as they were in the embodiments depicted in FIGS. 22-27. As depicted, the flexible electrode is a tapered brush electrode 74 since the distal band 130 is relatively smaller than the proximal band 132, which creates a narrowing, frustal-conical configuration for the compressible mesh 128. As the mesh is compressed (FIG. 30), the distal tip 82 of the tapered brush electrode 74 is driven toward the distal band 130 so as to be adjacent to the tissue to be ablated. Again, as the compressible mesh 128 is compressed, it may bulge as shown in FIG. 30. As mentioned in connection with FIGS. 22-27, the compressible mesh 128 at least partially shields the flexible electrode (e.g., the brush electrode 74) from the surrounding blood.

Compressible Bellows, Flexible Electrode Catheter [10th-12th Embodiments]

FIGS. 31-34 depict a tenth embodiment $10^J$ of the spring-tip, flexible electrode catheter according to the present invention. In this embodiment, a compressible bellows or corrugated shield 134 is present at the distal end 22 of the outer catheter sheath 20. FIG. 31 is a fragmentary, isometric view in partial cross section of this embodiment. Again, a brush electrode 12 is depicted in contact with a conductor 28 of ablative energy. In FIGS. 31, 33, and 34, the compressible bellows 134 is constructed from nonporous material (e.g., a nonporous, flexible polymer). In FIG. 32, the compressible bellows 134' is constructed from porous material. Whenever conductive or nonconductive fluid is present within the lumen 32 of the catheter, that fluid may seep through the porous compressible bellows 134' at a controlled or uncontrolled rate, depending upon the particular application.

As shown in, for example, FIG. 33, the compressible bellows comprises a distal edge or rim 136 and a proximal edge or rim 138. The proximal edge 138 of the compressible bellows 134 is adjacent to the distal end 22 of the outer catheter sheath 20. In FIG. 33, the compressible bellows is depicted in an uncompressed configuration. Thus, the exposed portion 42 of the brush electrode 12, which is the portion of the brush electrode extending past the distal end 22 of the outer catheter sheath 20, is residing within the compressible bellows with the working surface 44 of the brush electrode offset a maximum amount from the distal edge 136 of the compressible bellows 134.

In FIG. 34, which is a fragmentary view in partial cross section of the spring-tip, brush electrode catheter depicted in FIGS. 31 and 33, the compressible bellows 134 has been fully compressed. Thus, in the configuration depicted in FIG. 34, the working surface 44 (not visible in FIG. 34) at the distal end of the exposed portion 42 of the brush electrode 12 has moved adjacent to the distal edge 136 of the compressible bellows 134. Thus, the working surface 44 of the brush electrode would be adjacent to the tissue to be ablated. Therefore, when the distal edge 136 of the compressible bellows 134 is pressed against the tissue to be ablated, the working surface 44 of the brush electrode 12 is brought adjacent to that same tissue for delivery of the ablative energy.

Figure 35:
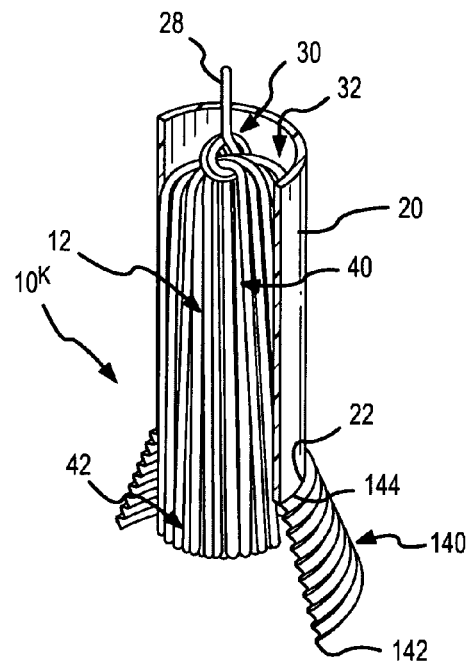
FIG. 35 is a fragmentary, isometric view in partial cross section of an eleventh embodiment of the spring-tip, brush electrode catheter according the present invention, having an outwardly-tapering, compressible bellows at the distal end of the catheter sheath.
Figure 36:
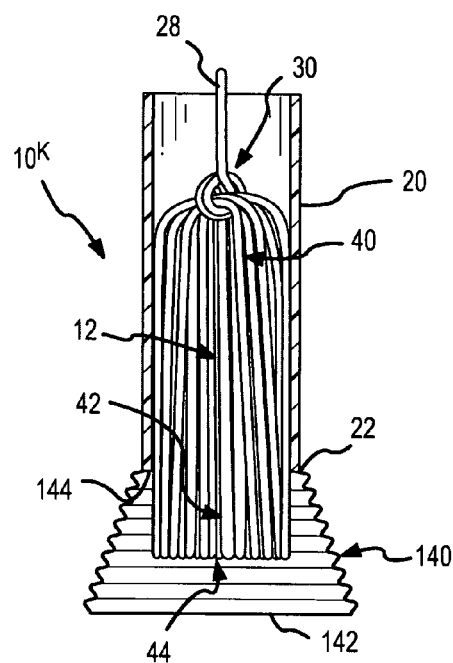
FIG. 36 is a fragmentary view in partial cross section of the spring-tip, brush electrode catheter depicted in FIG. 35 with the outwardly-tapering, compressible bellows in an uncompressed configuration.
Figure 37:
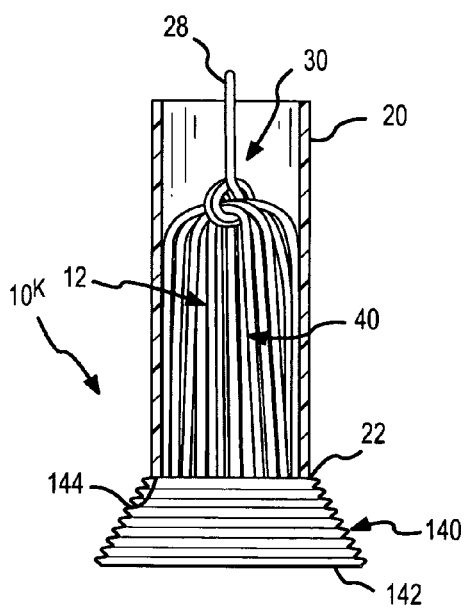
FIG. 37 is a fragmentary view in partial cross section of the spring-tip, brush electrode catheter depicted in FIGS. 35 and 36 with the outwardly-tapering, compressible bellows in a compressed configuration.

FIGS. 35-37 depict an eleventh embodiment $10^K$ of the spring-tip, flexible electrode catheter according to the present invention. As shown in FIG. 35, which is a fragmentary, isometric view in partial cross section, the eleventh embodiment comprises a spring-tip brush electrode catheter $10^K$ with an outwardly-tapering, compressible bellows 140 at the distal end 22 of the outer catheter sheath 20. The compressible bellows 140 depicted in FIGS. 35-37 includes a distal edge or rim 142 and a proximal edge or rim 144. The proximal edge 144 of the compressible bellows 140 is adjacent to the distal end 22 of the outer catheter sheath 20.

FIG. 36 is a fragmentary view in partial cross section of the spring-tip, brush electrode catheter $10^K$ depicted in FIG. 35 with the compressible bellows 140 in an uncompressed configuration. In this configuration, the working surface 44 of the brush electrode 12 is displaced its maximum distance from the distal edge 142 of the compressible bellows 140 and thus from the tissue to be ablated. In FIG. 37, which is a fragmentary view in partial cross section of the spring-tip, brush electrode catheter $10^K$ depicted in FIGS. 35 and 36, the compressible bellows 140 is in a fully-compressed configuration. Thus, in FIG. 37, the working surface 44 at the distal end of the brush electrode 12 is adjacent to the distal edge 142 of the compressible bellows 140 and is, therefore, also closely adjacent to the tissue to be ablated.

Figure 38:
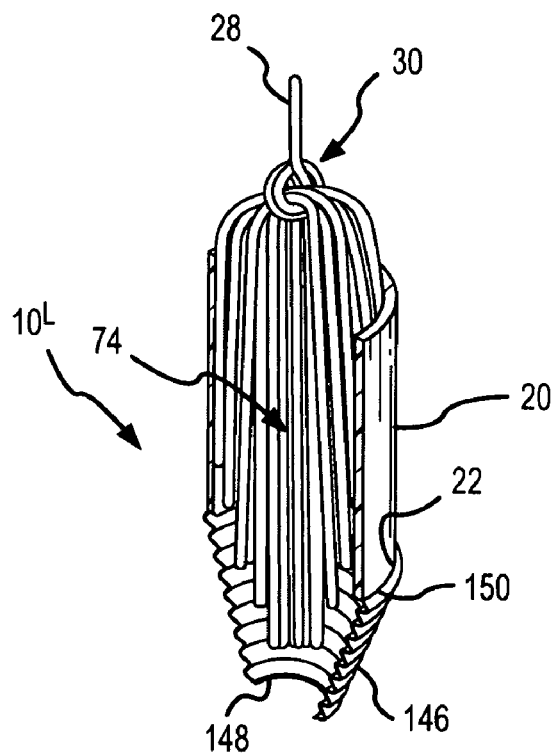
FIG. 38 is a fragmentary, isometric view in partial cross section of a twelfth embodiment of the spring-tip, brush electrode catheter according to the present invention, having an inwardly-tapering, compressible bellows at the distal end of the catheter sheath.
Figure 39:
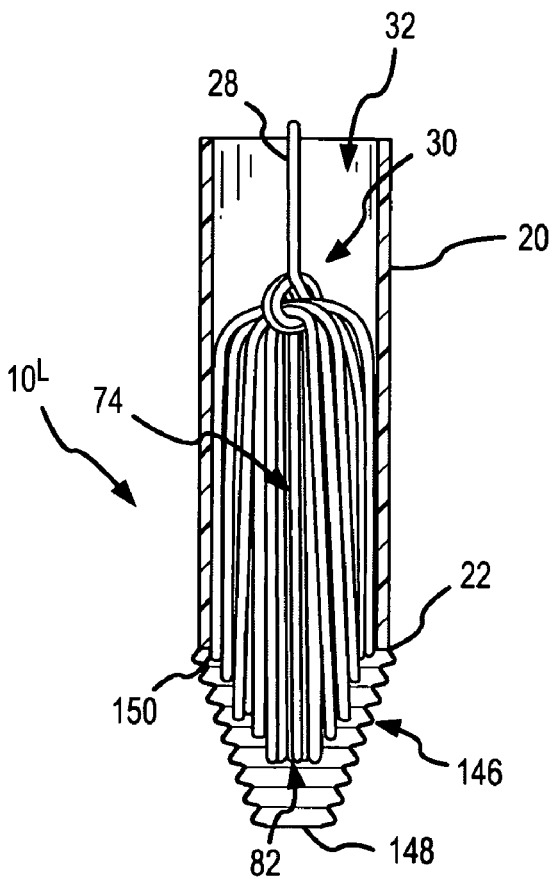
FIG. 39 is a fragmentary view in partial cross section of the spring-tip, brush electrode catheter depicted in FIG. 38 with the inwardly-tapering, compressible bellows in an uncompressed configuration.
Figure 40:
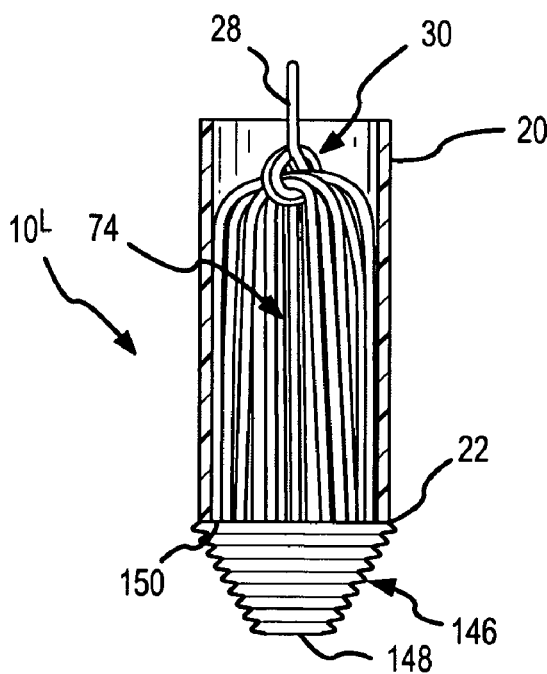
FIG. 40 is a fragmentary view in partial cross section of the spring-tip, brush electrode catheter depicted in FIGS. 38 and 39 with the inwardly-tapering, compressible bellows in a compressed configuration.

FIGS. 38-40 depict a twelfth embodiment $10^L$ of the spring-tip, flexible electrode catheter according to the present invention. In this embodiment, an inwardly-tapering, compressible bellows 146 is present at the distal end 22 of the outer catheter sheath 20. The inwardly-tapering, compressible bellows 146 comprises a distal edge or rim 148 and a proximal edge or rim 150. The proximal edge 150 of the compressible bellows 146 is adjacent to the distal end 22 of the outer catheter sheath 20. A tapered brush electrode 74 (previously described in connection with FIGS. 10-12, 19-21, and 28-30) may be used when an inwardly-tapering, compressible bellows 146 is present at the distal end 22 of the outer catheter 20. The tapered brush electrode 74 includes a distal tip 82 defining at least a portion of the working surface of the brush electrode 74. The brush filaments may be trimmed or shaped to roughly approximate the shape of the inner surface of the inwardly-tapering, compressible bellows 146.

As shown in FIG. 39, which is a fragmentary view in partial cross section of the spring-tip, brush electrode catheter $10^L$ depicted in FIG. 38, when the inwardly-tapering, compressible bellows 146 is in an uncompressed configuration, the distal tip 82 and working surface of the tapered brush, electrode 74 is offset from the distal edge 148 of the compressible bellows 146.

FIG. 40 is a fragmentary view in partial cross section of the spring-tip, brush electrode catheter $10^L$ depicted in FIGS. 38 and 39 with the compressible bellows 146 in a compressed configuration. When the bellows are compressed as shown in FIG. 40, the distal tip 82 and working surface of the tapered brush electrode 74 is adjacent to the distal edge 148 of the inwardly-tapering, compressible bellows 146. Thus, the distal tip 82 and working surface of the tapered brush electrode 74 is also adjacent the tissue that is to be ablated.

The compressible bellows (134, 134', 140, 146) depicted in FIGS. 31-40 shields the flexible electrode (e.g., the brush electrode 12 or 74) from the surrounding blood, and thus helps inhibit the formation of undesirable coagulum.

Stand-Off, Spring-Tip, Flexible Electrode Catheter [13th Embodiment]

Figure 41:
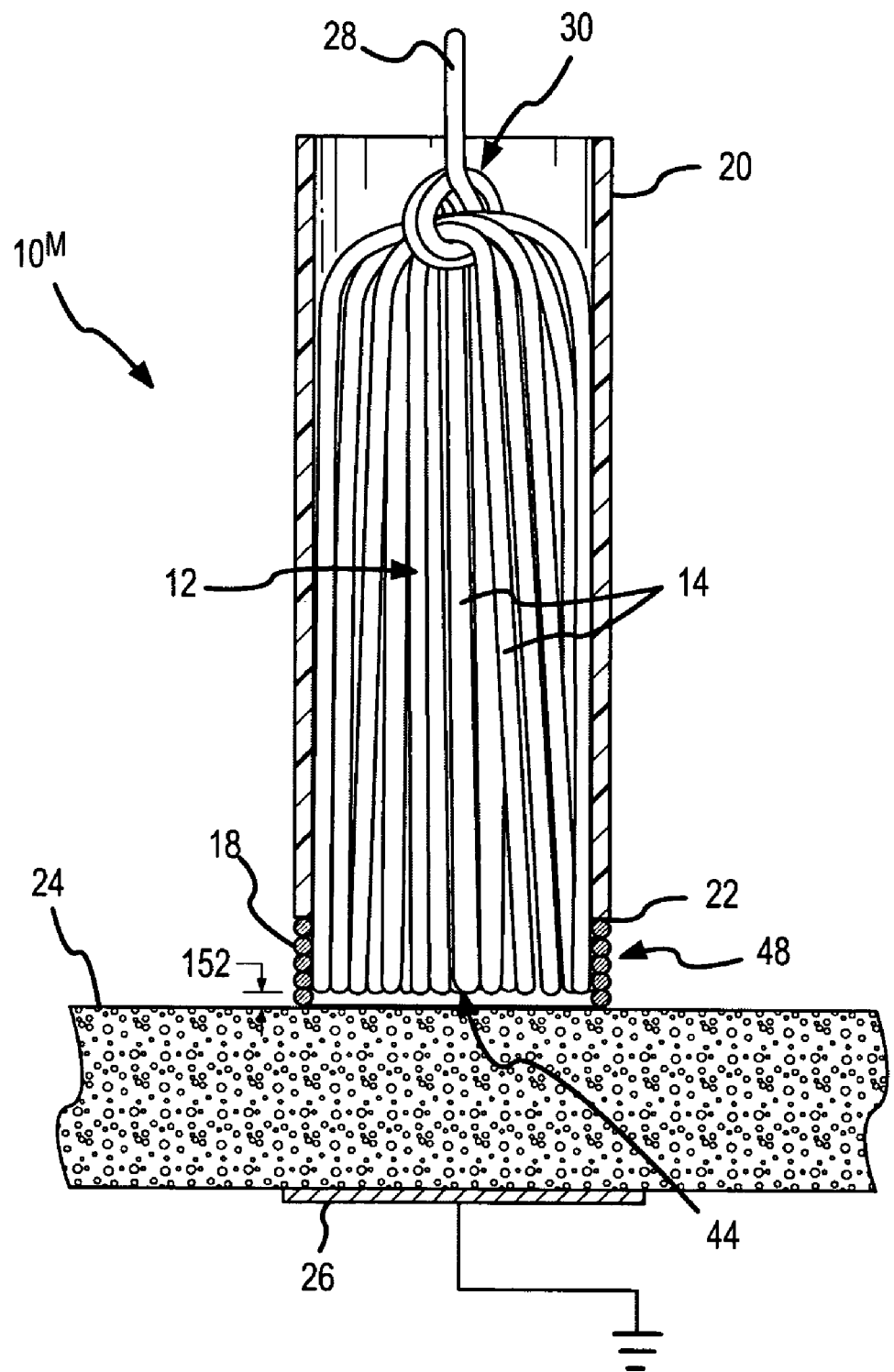
FIG. 41 is a fragmentary view in partial cross section of a spring-tip, brush electrode catheter according to a thirteenth embodiment of the present invention, which is similar to the first embodiment as depicted in FIG. 3, but having a standoff distance between the distal ends of the brush filaments and the tissue to be ablated.

FIG. 41 depicts a thirteenth embodiment $10^M$ of the spring-tip, flexible electrode catheter according to the present invention, which is a stand-off, spring-tip, flexible electrode catheter. This embodiment is similar to the first embodiment $10^A$ as depicted in FIG. 3, but the distal end of the brush electrode 12 has been trimmed (or the brush filaments 14 have been positioned within the outer sheath 20) so that the working surface 44 remains out of direct contact with the tissue 24 even when the coil spring 18 is fully compressed as shown in FIG. 41. Thus, when the spring coils are stacked to form the cylindrical shield 48, the working surface 44 of the brush electrode 12 remains offset from the tissue 24 to be ablated by a stand-off distance 152, which may be selected based upon the particular type of ablation being performed.

Although FIG. 41 depicts a round-wire, coil spring 18 with no taper (similar to the coil spring depicted in FIGS. 1-5), any of the springs depicted in any of the drawings could be used in this stand-off configuration, including outwardly-tapering or inwardly-tapering springs; round-wire, coil springs; flat-wire, coil springs; tapering or nontapering compressible mesh; and tapering or nontapering compressible bellows.

Embedded-Spring, Flexible Electrode Catheter [14th Embodiment]

Figure 42:
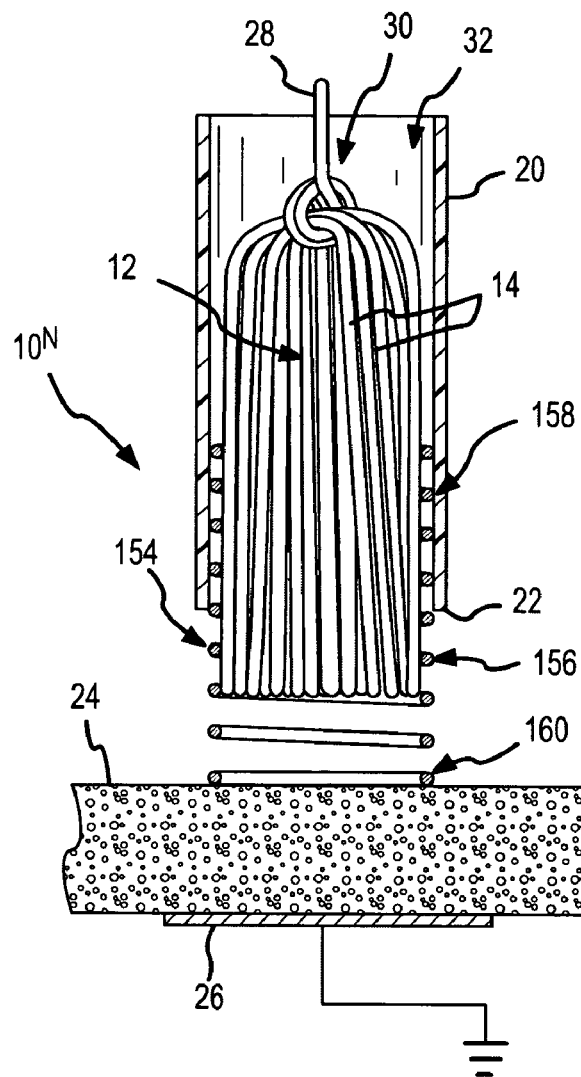
FIG. 42 is a fragmentary view in partial cross section of a spring-tip, brush electrode catheter according to a fourteenth embodiment of the present invention, having an embedded spring at the distal end of the catheter sheath.
Figure 43:
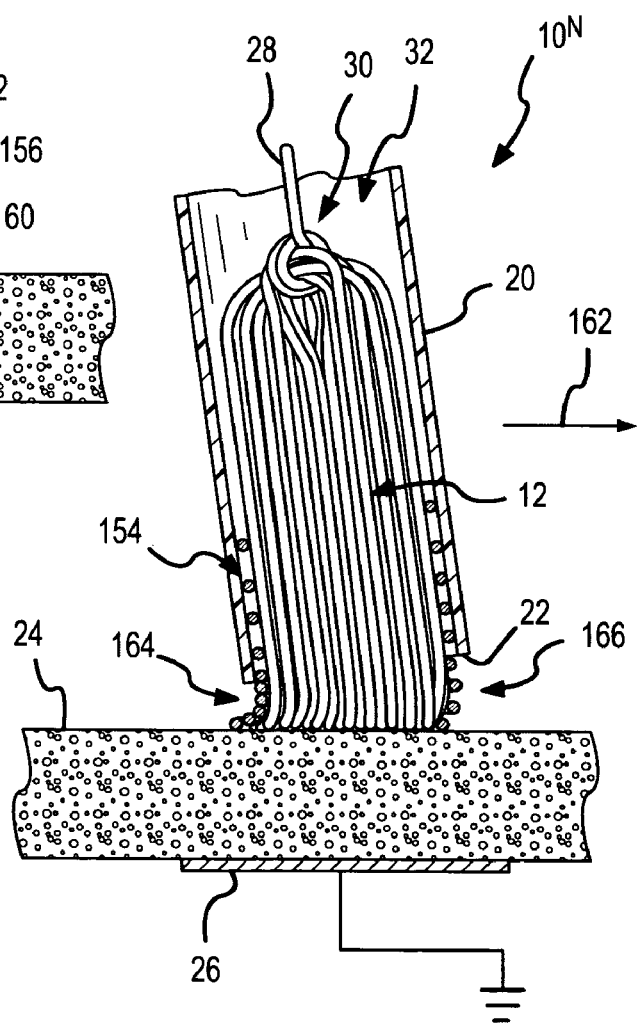
FIG. 43 depicts the spring-tip, brush electrode catheter of FIG. 42 with the spring under compression and the brush electrode in motion across the tissue being ablated, with the catheter sheath leaning away from the direction of travel.
Figure 44:
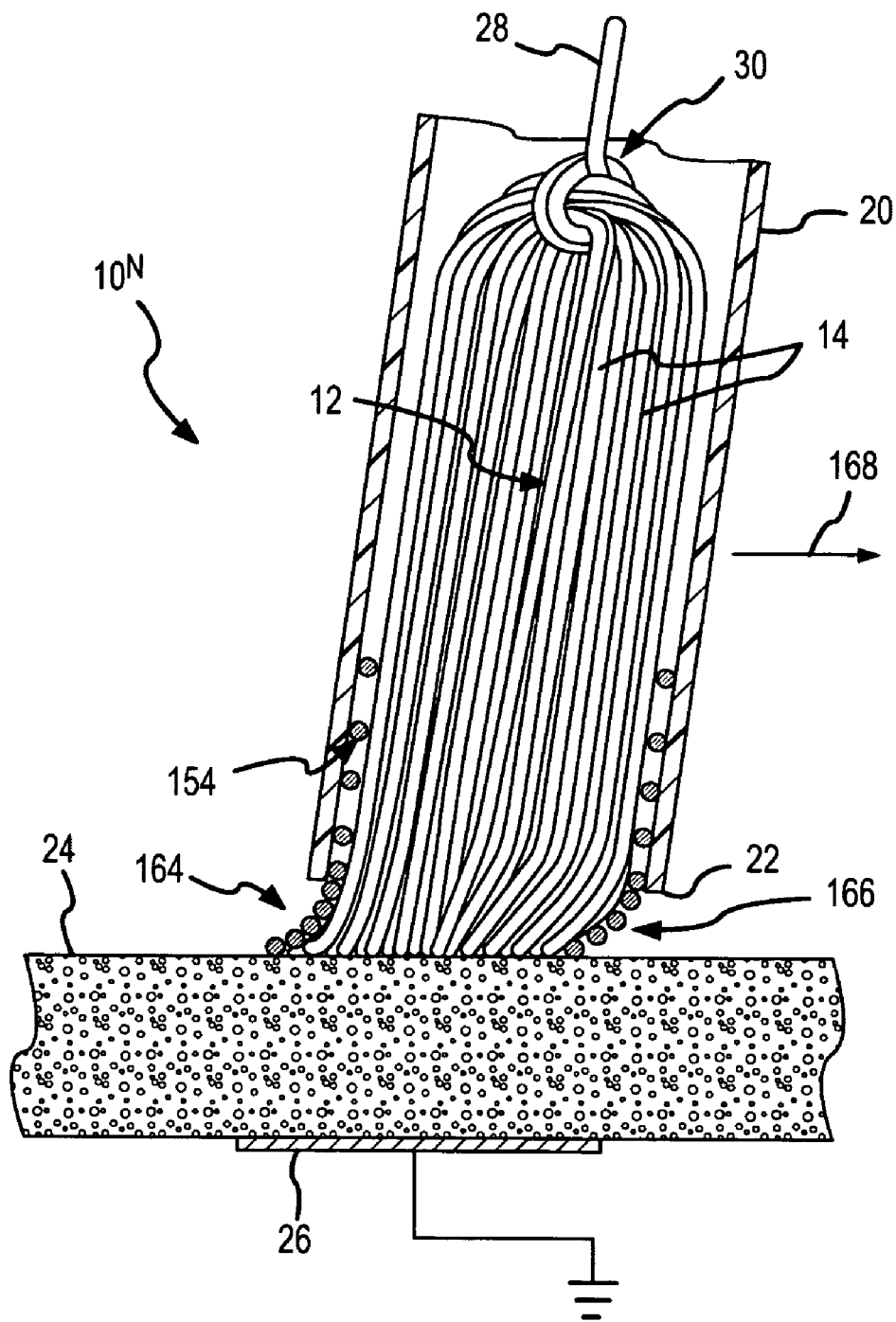
FIG. 44 depicts the spring-tip, brush electrode catheter of FIG. 42 with the spring under compression and the brush electrode in motion across the tissue being ablated, with the catheter sheath leaning toward the direction of travel.

FIGS. 42-44 depict a fourteenth embodiment $10^N$ of the present invention, which has an embedded spring 154 at the distal end 22 of the catheter sheath 20. As shown in FIG. 42, which is a fragmentary view in partial cross section of the spring-tip, brush electrode catheter $10^N$ according to the fourteenth embodiment of the present invention, the embedded, round-wire, coil spring 154 comprises an exposed section 156 and an embedded section 158. The exposed section 156 of round-wire, coil spring 154 is the section of the embedded, round-wire, coil spring 154 that extends from the distal end 22 of the outer catheter sheath 20 to a distal end 160 of the coil spring 154. The embedded section 158 of the round-wire, coil spring 154 extends within the lumen 32 of the outer catheter sheath 20. The embedded section 158 could, alternatively, be partially or fully molded into the catheter sheath material itself.

In FIG. 43, the embedded, coil spring 154 is under compression, and the spring-tip, brush electrode catheter $10^N$ is moving in the direction of arrow 162 across the tissue 24 that is being ablated. Similar to what is depicted in FIG. 4, the catheter sheath 20 is leaning away from the direction of travel 162, which indicates that the spring-tip, brush electrode catheter $10^N$ is being pushed across the tissue 24 during the formation of a linear lesion. The embedded, round-wire, coil spring 154 has a trailing surface 164 and a leading surface 166 during this movement across the tissue 24. As previously discussed, the trailing surface 164 may comprise stacked spring coils that help shield the brush electrode 12 from the surrounding blood. As also discussed above, the leading surface 166 may be "leaky" to permit any conductive or nonconductive fluid flowing through the lumen 32 of the outer catheter sheath 20 to impinge upon the tissue prior the delivery of ablation energy to the tissue.

FIG. 44 is similar to FIG. 43 and shows the spring-tip, brush electrode catheter $10^N$ moving in the direction of arrow 168 across the tissue 24 that is being ablated. Since the catheter sheath 20 is leaning toward the direction of travel 168, the spring-tip, brush electrode catheter $10^N$ is being dragged across the tissue 24 during the formation of a linear lesion in FIG. 44 (compare FIG. 5).

In the embodiment depicted in FIGS. 42-44, the "spring-tip" is shown as comprising a round-wire, coil spring 154 with no taper that is embedded in the distal end 22 of the outer sheath 20. Any of the springs depicted in any of the drawings could be used in this embedded-spring configuration, including outwardly-tapering or inwardly-tapering springs; round-wire, coil springs; flat-wire, coil springs; tapering or nontapering compressible mesh (see FIGS. 22-30); and tapering or nontapering compressible bellows (see FIGS. 31-40). As depicted in FIGS. 43 and 44, the embedded spring may be configured so that the trailing surface 164 of the shield formed by the coils around the brush electrode 12 permits only minimal contact between the brush electrode and the surrounding blood, whereas the leading surface 166 permits any conductive or nonconductive fluid traveling within the lumen to exit the shield ahead of the moving spring-tip, brush electrode catheter $10^N$ so that it may impinge upon the tissue 24 prior to actual ablation.

Spring-Tip Flexible Electrode Catheter Having Extended Brush Filaments [15th Embodiment]

Figures 45, 46:
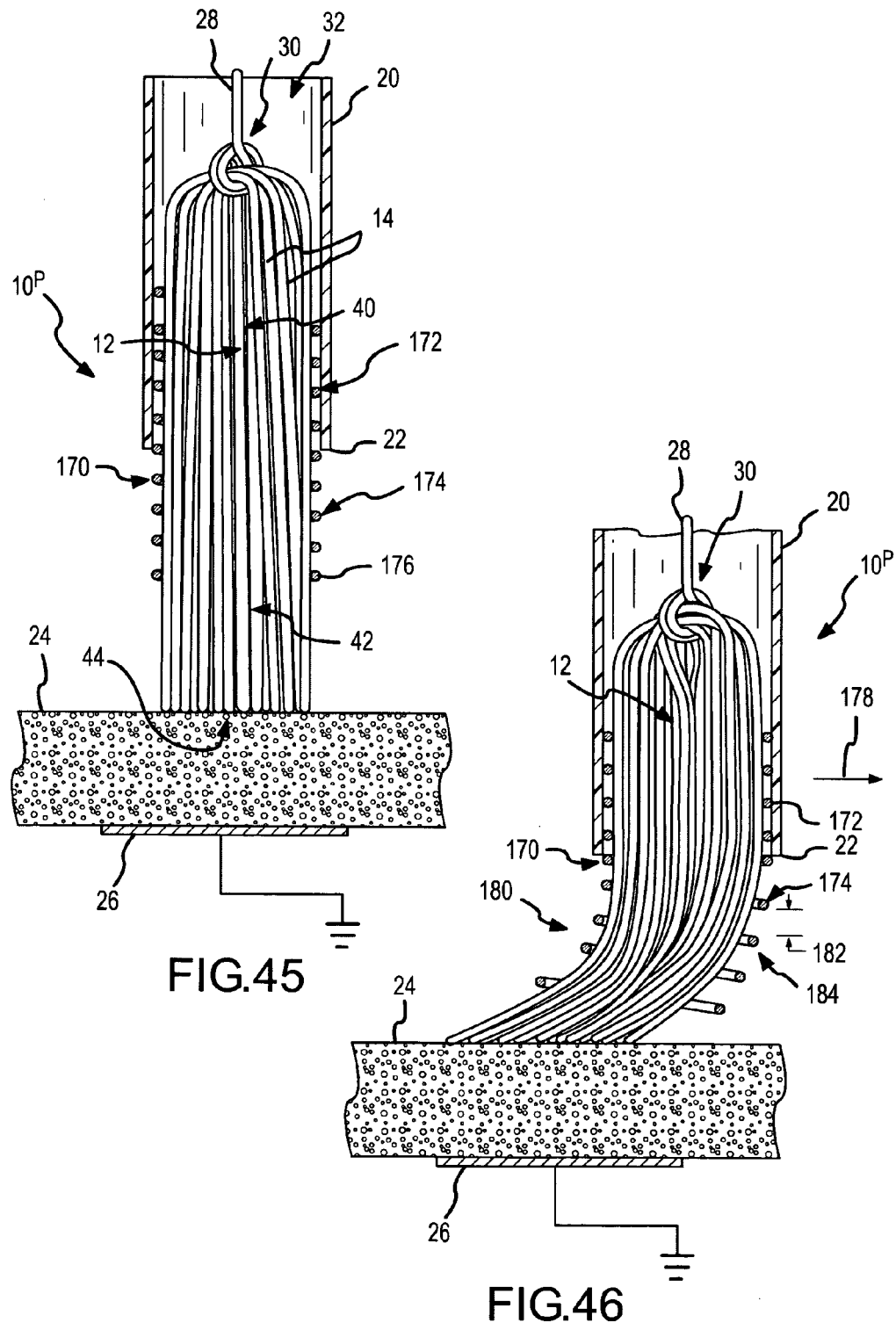
FIG. 45 is a fragmentary view in partial cross section of a spring-tip, brush electrode catheter according to a fifteenth embodiment of the present invention, having brush filaments extending past a distal end of the uncompressed spring.
FIG. 46 depicts the spring-tip, brush electrode catheter of FIG. 45 in motion across the tissue being ablated.

FIGS. 45 and 46 depict a spring-tip, flexible electrode catheter according to a fifteenth embodiment $10^P$ of the present invention. An embedded, coil spring 170 again comprises an embedded section 172 and an exposed section 174. In this embodiment, the spring-tip, flexible electrode catheter $10^P$ comprises a brush electrode 12 having extended brush filaments 14. The extended brush filaments comprise an embedded portion 40 and an exposed portion 42. Part of the exposed portion 42 of the extended brush filaments extends past the distal end 22 of the outer sheath 20, and part of the exposed portion 42 of the extended brush filaments extends past a distal end 176 of the uncompressed spring 170. In particular, the distal ends of the brush filaments 14 extend past the distal end 176 of the uncompressed spring 170. The spring 170 is shown in FIGS. 45 and 46 as an embedded, round-wire, coil spring with no taper that is embedded into the distal end 22 of the outer sheath 20. Again, the spring could be partially or fully embedded into the outer sheath material itself, and the spring does not have to be a round-wire, coil spring. In the configuration depicted in FIG. 45, a working surface 44 comprising the distal ends of the brush filaments 14 is in contact with the tissue 24. Thus, the spring-tip, brush electrode catheter $10^P$ may be forming a spot lesion.

In FIG. 46, the spring-tip, flexible electrode catheter $10^P$ is moving in the direction of arrow 178 across the surface of the tissue 24 to form a linear lesion. The exposed section 174 of the embedded, coil spring 170 is being skewed by this motion. A trailing surface 180 of the exposed section 174 of coil spring 170 presents somewhat smaller coil separation 182 than is present on a leading surface 184 of the exposed section 174 of the embedded, coil spring 170. Again, the coil spring depicted in FIGS. 45 and 46 could be replaced by an outwardly-tapering spring, an inwardly-tapering spring, or any other type of spring disclosed herein, including compressible mesh springs and compressible bellows springs.

Booted, Spring-Tip, Flexible Electrode Catheter [16th-18th Embodiments]

Figure 47:
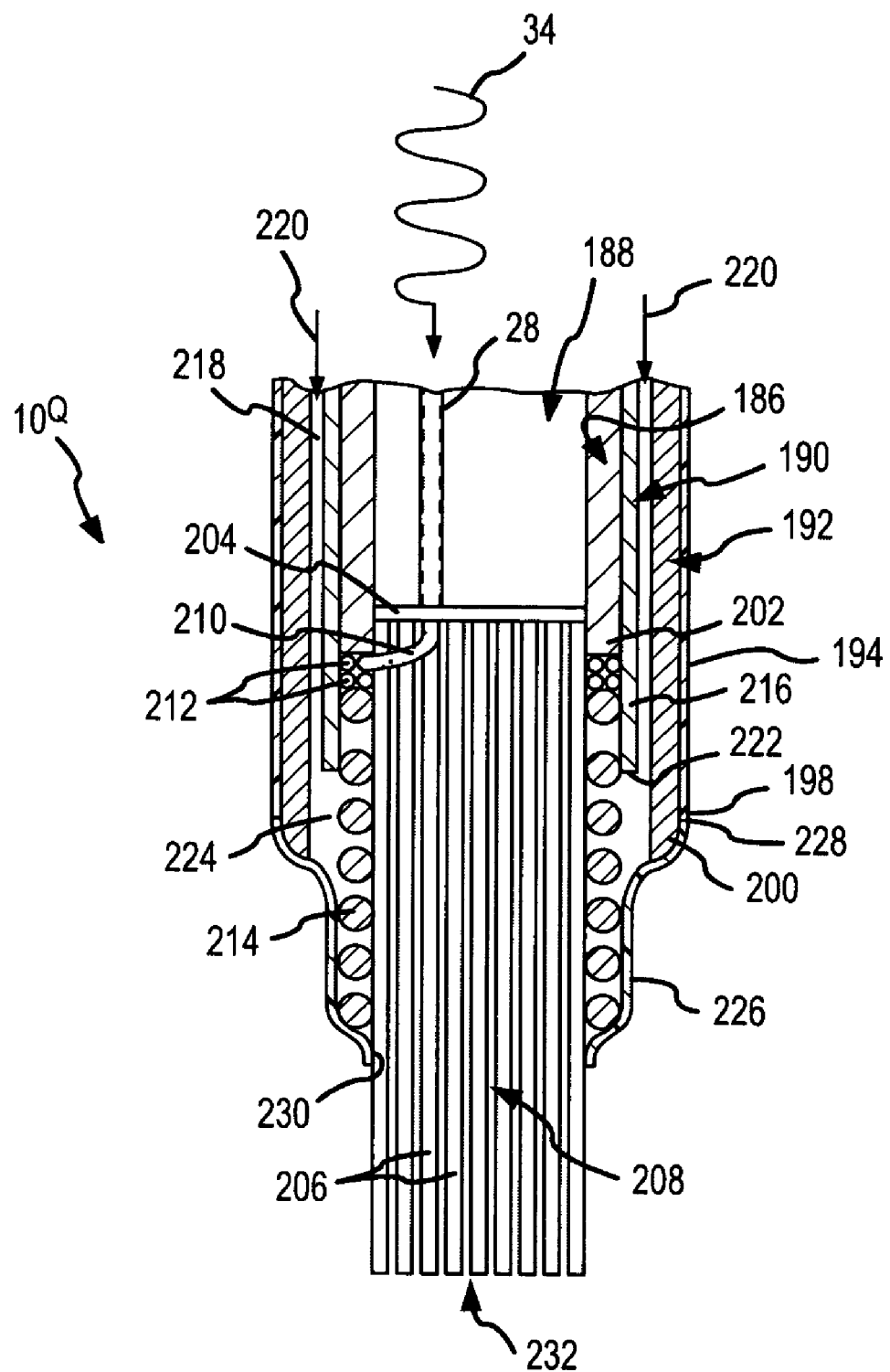
FIG. 47 is a fragmentary view in partial cross section of a spring-tip, brush electrode catheter according to a sixteenth embodiment of the present invention, having a nipple or shield around the spring at the distal end of the catheter.

FIG. 47 is a fragmentary view in partial cross section of a spring-tip, flexible electrode catheter according to a sixteenth embodiment $10^Q$ of the present invention. This embodiment is a booted, spring-tip, flexible electrode catheter. In this embodiment, there is an inner sheath 186, which defines a lumen 188; an intermediate sheath 190; and an outer sheath 192. A lubricious outer wall 194 envelopes the outer sheath 192. The lubricious outer wall terminates at a distal edge 198 adjacent to a distal end 200 of the outer sheath 192. The inner sheath 186 comprises a distal end 202 that supports a mechanical interface 204, which, in turn, supports the filaments 206 of a brush electrode 208.

Ablative energy 34 is introduced to the brush electrode 208 through a conductor 28 located within the lumen 188 of the inner sheath 186 in the configuration depicted in FIG. 47. In particular, an uninsulated portion 210 of the conductor 28 passes through the mechanical interface 204 before it is wrapped around the outer surface of the bundle of brush filaments 206 to form loops or coils 212 that are in contact with the round-wire, coil spring 214 that also surrounds the bundle of brush filaments 206. In the configuration depicted in FIG. 47, the loops or coils 212 of uninsulated conductor are positioned between the distal end 202 of the inner sheath 186 and the most proximal coil of the round-wire, coil spring 214.

A distal portion 216 of the intermediate sheath 190 supports the outer circumference of the loops or coils 212 of uninsulated conductor 210, and the distal portion 216 of the intermediate sheath 190 also supports the proximal end of the round-wire, coil spring 214. An annular gap or channel 218 is defined between the intermediate sheath 190 and the outer sheath 192. When conductive or nonconductive fluid is used in conjunction with the spring-tip, brush electrode catheter $10^Q$ depicted in FIG. 47, that fluid travels in the annular gap 218 in the fluid flow direction indicated by the arrows 220. The intermediate sheath 190 includes a distal end 222 that is longitudinally offset from the distal end 200 of the outer sheath 192, thereby forming an annular fluid jacket 224 between an inner surface of the outer sheath and an outer surface of the brush electrode. Fluid traveling in the annular gap 218 between the intermediate sheath 190 and the outer sheath 192 ultimately reaches the annular fluid jacket 224. From the annular fluid jacket 224, the fluid is introduced to the interstitial gaps between the brush filaments 206 through the coils of the round-wire, coil spring 214.

A smooth, flexible polymer nipple or boot 226 extends from an annular juncture 228 at the distal end 198 of the lubricious outer wall 194 to a ring of contact 230 at the distal edge of the polymer nipple 226. Since the ring of contact 230 makes circumferential contact with the outer surface of the bundle of brush filaments comprising the brush electrode 208, the fluid flowing through the annular gap 218, into the annular fluid jacket 224, through the coil spring 214, and into the interstitial gaps between the brush filaments 206, is prevented from immediately exiting the brush electrode 208 radially and is directed toward the working surface 232 of the brush electrode 208.

Figure 48:
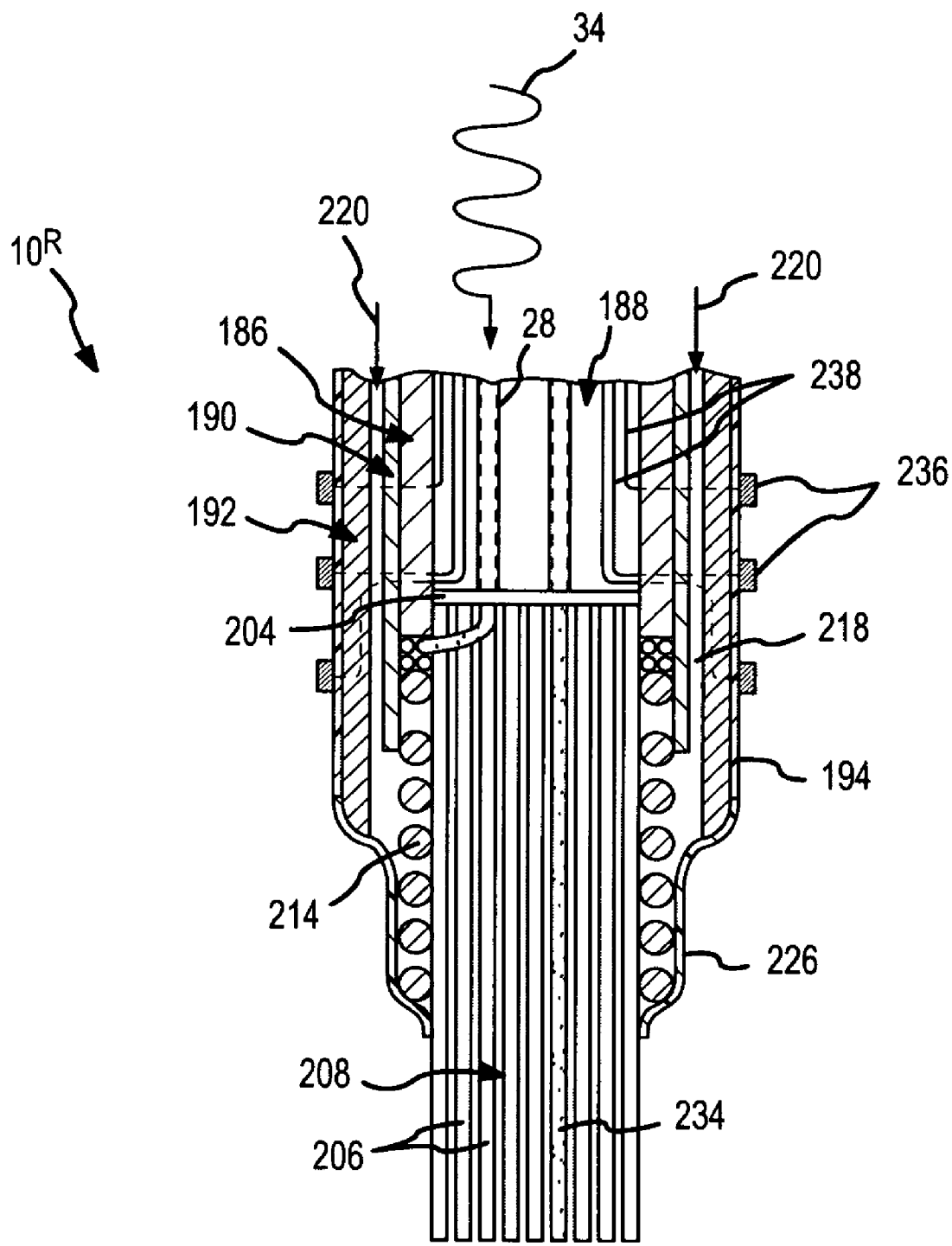
FIG. 48 is a fragmentary view in partial cross section of a spring-tip, brush electrode catheter according to a seventeenth embodiment of the present invention, which is similar to the embodiment depicted in FIG. 47, but includes a secondary lead embedded among the brush filaments and sensors or markers adjacent to the distal end of the catheter.

FIG. 48 is a fragmentary view in partial cross section of a spring-tip, flexible electrode catheter according to a seventeenth embodiment $10^R$ of the present invention. This embodiment is similar to the embodiment depicted in FIG.

47, but includes a couple of additional features. A secondary lead 234 is present within the lumen 188 of the inner sheath. This secondary lead may pass through the mechanical interface 204 and become embedded among the other brush filaments 206. As described in the '919 application that has been incorporated by reference as though fully set forth herein, this secondary lead 234 may provide power to, or a communication link for, some type of sensor embedded among the brush filaments 206. A plurality of diagnostic sensors or markers 236 are also depicted in the embodiment of FIG. 48 adjacent to the distal end of the catheter. Diagnostic leads 238 are present to carry signals to and from the diagnostic sensors or markers 236. For protection, these diagnostic leads 238 may travel within the lumen 188 of the inner sheath 186.

Figure 49:
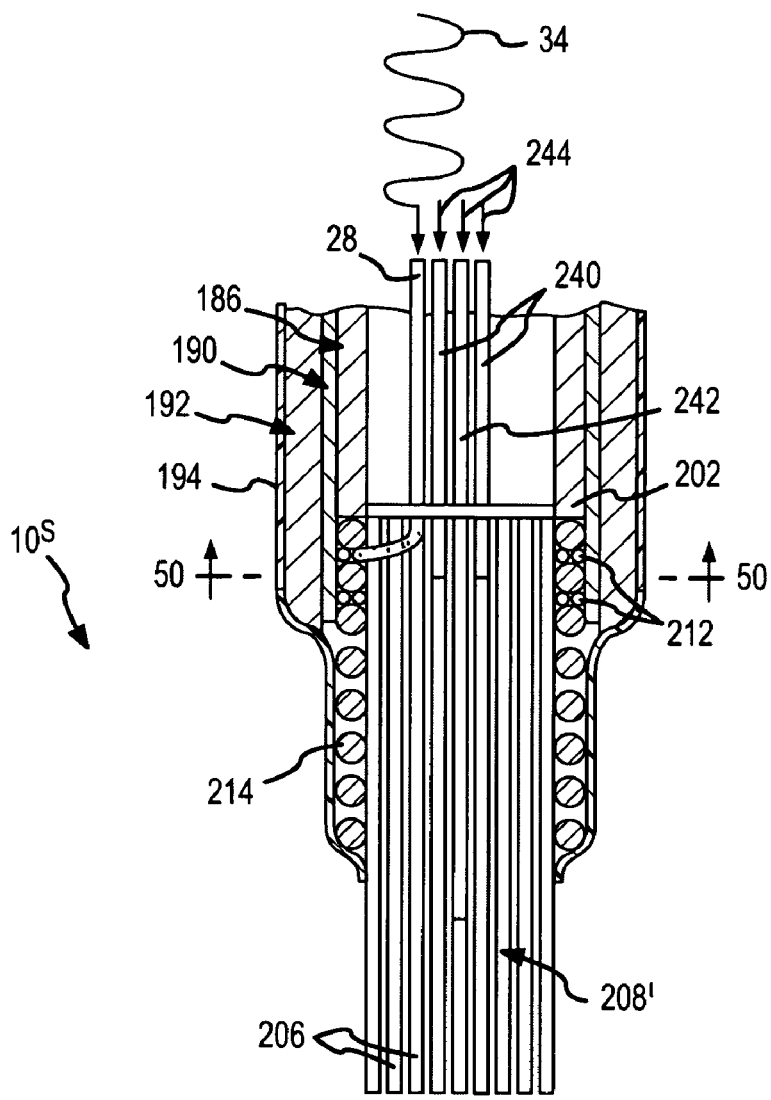
FIG. 49 is a fragmentary view in partial cross section of a spring-tip, brush electrode catheter according to an eighteenth embodiment of the present invention, which is similar to the embodiment depicted in FIG. 47, but includes a plurality of hollow filaments that deliver conductive or nonconductive fluid to the brush filaments.
Figure 50:
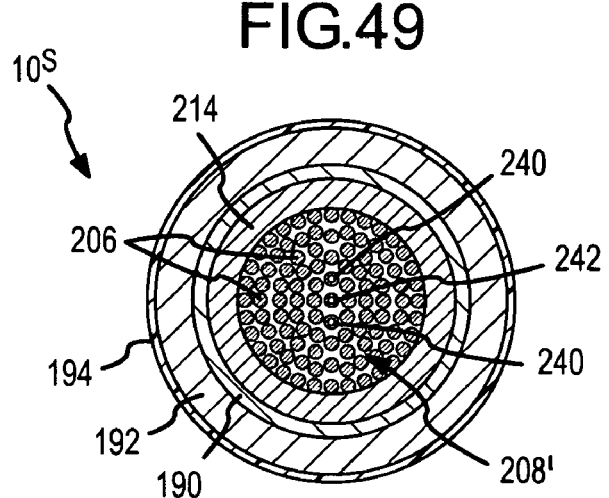
FIG. 50 is a cross-sectional view taken along line 50-50 of FIG. 49, depicting the hollow filaments embedded among the brush filaments.

FIGS. 49 and 50 depict a spring-tip, flexible electrode catheter according to an eighteenth embodiment $10^S$ of the present invention. In this embodiment, the inner sheath 186, the intermediate sheath 190, and the outer sheath 192 are collapsed upon each other, thereby removing the annular channel 218 that may be seen in the embodiments of FIGS. 47 and 48. In the embodiment of FIGS. 49 and 50, a plurality of hollow filaments are present to deliver conductive or nonconductive fluid to the brush filaments 206. In the embodiment depicted in FIG. 49, three hollow filaments are present including two short hollow filaments 240 and one medium length hollow filament 242. These hollow filaments 240, 242 are adapted to carry conductive or nonconductive fluid flowing along the fluid flow direction indicated by the arrows 244 to the brush filaments 206. FIG. 50 is a cross sectional view taken along line 50-50 of FIG. 49 and clearly depicts the three hollow filaments 240, 242 embedded among the conductive or nonconductive filaments 206 comprising the brush electrode 208'. FIG. 49 also shows a slightly different configuration for the loops or coils 212 that deliver ablative energy 34. In particular, FIG. 49 shows the loops or coils 212 being wrapped among the spring coils rather than being pinched between the distal end 202 of the inner sheath 186 and the proximal end of the round-wire, coil spring 214.

As with the other embodiments described above, the non-tapering, round-wire coil spring 214 depicted in FIGS. 47-49 could be replaced with other spring types (e.g., flat wire, mesh, or bellows), and the spring, whether, for example, a round-wire coil, a flat-wire coil, or a compressible bellows, could also be tapered as shown in FIGS. 6-12, 16-21, 25-30, and 35-40. The spring could also be embedded into the distal end 202 of, for example, the inner sheath 186 (i.e., it could be embedded into the sheath material itself).

Method of Use

When the spring-tip, flexible electrode catheter (e.g., $10^4$ in FIGS. 1-5 and 51) is placed against the tissue 24, the spring tip improves the efficacy of tissue ablation in at least the following ways: (i) by providing an axial suspension for the flexible electrode (e.g., the brush filaments 12 in FIG. 51) when it is placed at close-to-normal incidence to the tissue 24 to be ablated; (ii) by providing adequate contact pressure between the flexible electrode and the tissue when (a) the flexible electrode is placed at close-to-grazing incidence, or when (b) the flexible electrode is dragged on the tissue to make to a linear lesion; and (iii) by providing a mechanical shield that prevents the flexible brush filaments from splaying undesirably when pressed against the tissue (excessive splaying of the brush filaments 14 reduces the electric field at the brush-tissue interface and affects lesion formation). At low axial loading and, thus, low contact pressure between the spring-tip, flexible electrode and the tissue, the spring may be used to provide a desired standoff distance between the electrode and the tissue surface. At moderate axial loading and, thus, moderate contact pressure between the spring-tip, flexible electrode and the tissue, the distal tip of the electrode just touches the surface of the tissue. At high axial loading and, thus, high contact pressure between the spring-tip, flexible electrode and the tissue, the spring is fully compressed and allows only a predetermined depth of penetration of the distal tip of the electrode into the tissue 24.

Figure 51:
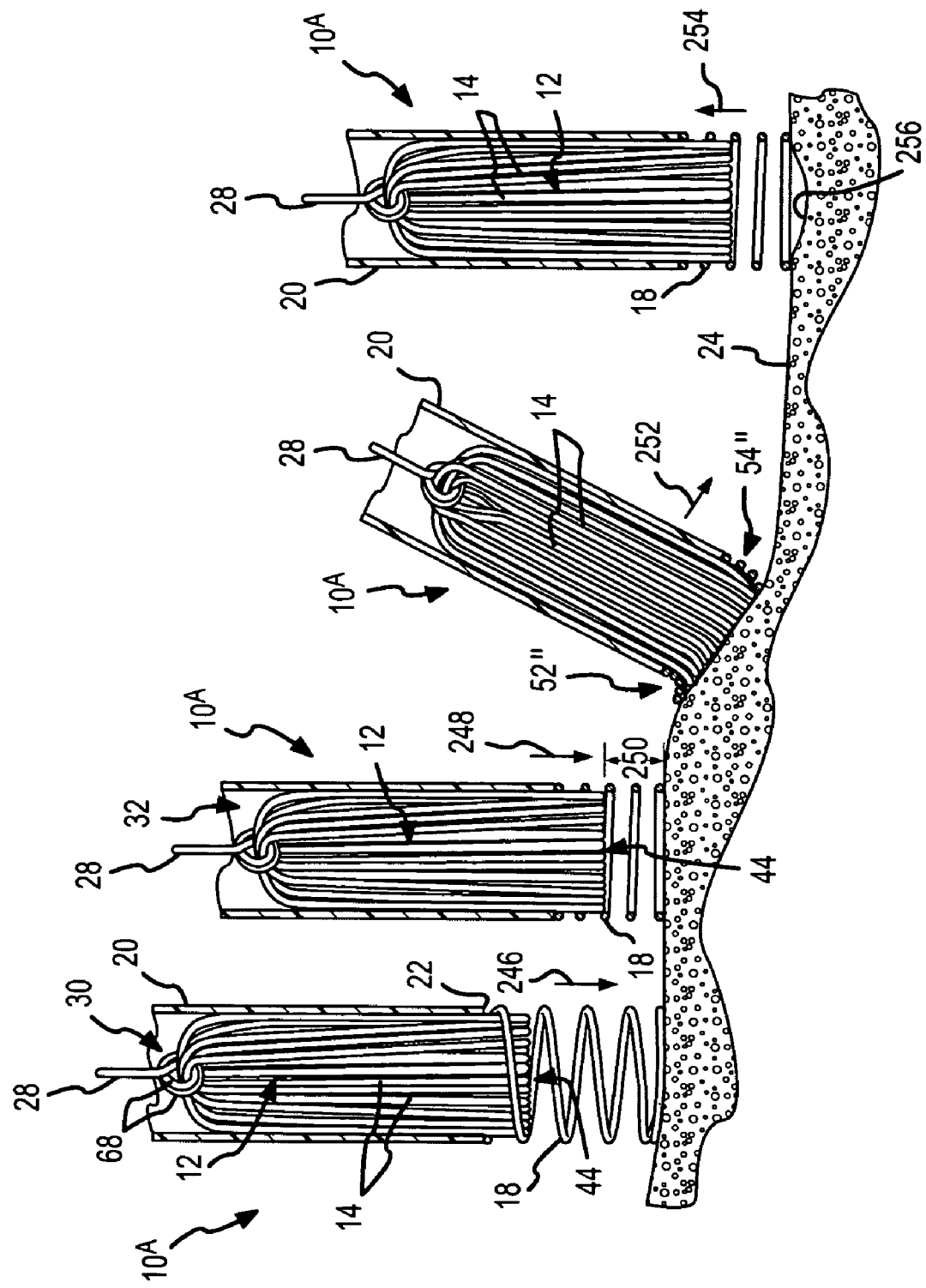
FIG. 51 depicts the spring-tip, brush electrode catheter of FIGS. 1-5 in a series of configurations during use of this embodiment of the spring-tip, flexible electrode catheter to ablate tissue.

FIG. 51 depicts the spring-tip, brush electrode catheter $10^A$ of FIGS. 1-5 in a series of stages during use of this embodiment of the spring-tip, flexible electrode catheter to ablate tissue 24. In particular, four possible stages of use are shown. In stages one and two (i.e., the two left images in FIG. 51), axial loading is used to compress the spring 18. In stage one, which is the leftmost image in FIG. 51, minimal axial loading has been applied, and the spring-tip, brush electrode catheter $10^4$ has just made contact with the tissue 24 to be ablated. As the spring 18 is compressed in the direction of arrow 246 under the influence of increased axial loading, the working surface 44 at the distal end of the brush electrode 12 is pressed toward the tissue 24. At stage two, which is depicted in the image that is second from the left in FIG. 51, the axial loading has further compressed the spring 18 in the direction of arrow 248, thereby bringing the working surface 44 of the brush electrode even closer to the tissue 24. Under this relatively low axial load, the spring 18 provides a standoff distance 250 between the working surface 44 of brush electrode 12 and the tissue surface. At this point, ablative energy 34 (see, e.g., FIG. 49) may be applied to the tissue 24.

In the third image from the left in FIG. 51, which is similar to what is shown in FIGS. 4 and 5, the coil spring 18 has been fully compressed and translation of the brush electrode 12 over the surface of the tissue 24 has commenced in the direction of arrow 252. As previously described, the trailing surface 52" of the compressed coil spring 18 comprises stacked coils that inhibit access to the brush filaments 14 by any surrounding blood. The leading surface 54" of the compressed coil spring 18 includes gaps between adjacent spring coils that allow conductive or nonconductive fluid flowing axially through the lumen 32 of the catheter to impinge upon the tissue 24 prior to ablation. As shown in this third stage, the catheter sheath 20 is substantially perpendicular to the tissue 24, which is an alternative orientation during translation from what is shown in FIGS. 4 and 5. In the rightmost view in FIG. 51, ablation is complete, translation has stopped, and the axial load is being removed from the catheter to allow the spring 18 to expand in direction of arrow 254, thereby removing the brush electrode 12 from the tissue 24. A lesion 256 may be seen on the tissue 24 in the rightmost view of FIG. 51. At this point, the spring-tip, flexible electrode catheter $10^4$ could be extracted.

Figure 52:
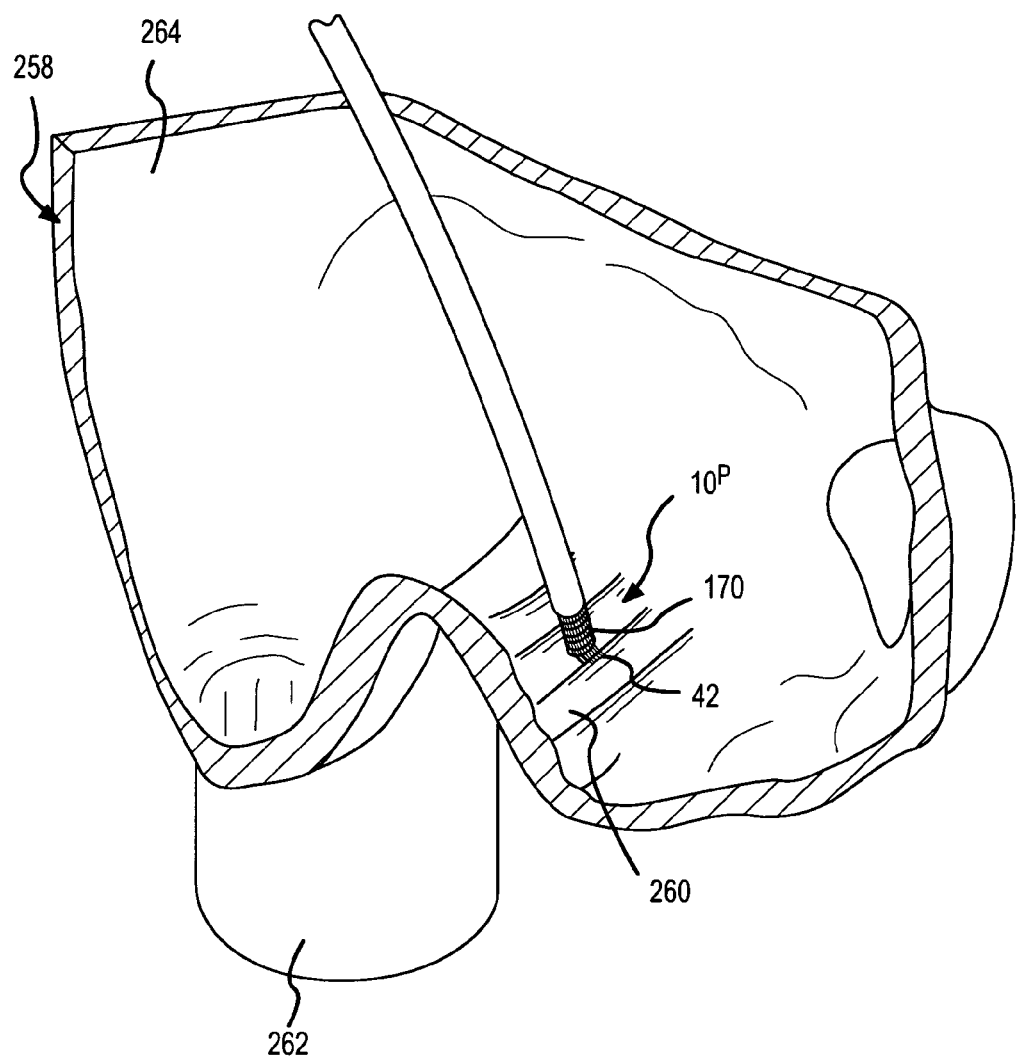
FIG. 52 is a schematic, cross-sectional view of the spring-tip, brush electrode catheter of FIGS. 45 and 46 being used with a catheter to ablate tissue within a heart.

FIG. 52 is an isometric view that schematically depicts the spring-tip, brush electrode catheter $10^P$ of FIGS. 45 and 46 being used with a catheter to ablate tissue within a heart 258. In particular, this figure schematically depicts ablation of a contoured or trabeculated surface 260 adjacent to the inferior vena cava 262 of the heart in the right atrium 264.

The spring-tip, flexible electrode catheter of the present invention provides a number of advantages, including, for example, the ability to form deep lesions in tissue while reducing the formation of undesirable coagulum and charring of the surface tissue, while applying a reasonable amount of RF energy, while mitigating electrode-tissue contact problems, and/or while reducing the amount of conductive fluid (e.g., saline) possibly entering a patient's bloodstream during the procedure. The present invention facilitates the formation of a deep lesion in a shorter period of time than is required by other existing ablation devices, and it provides the ability to create lesions in highly perfused tissue or in fluid-rich environments. The spring-tip, flexible electrode catheter facilitates enhanced tissue contact in difficult environments (e.g., during ablation of a contoured or trabeculated surface 260 (FIG. 52) inside a beating heart), whether creating a spot lesion or a continuous linear lesion, since the flexible electrode readily conforms to surface contours, while the bending stress of the spring enhances the contact pressure on the tissue.

Although several embodiments of this invention have been described above with a certain degree of particularity, those skilled in the art could make numerous alterations to the disclosed embodiments without departing from the spirit or scope of this invention. All directional references are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit or scope of the invention as defined in the appended claims. For example, in a possible alternative embodiment related to what is shown in FIGS. 1-5, a spring with a smaller radial diameter (not shown) may be embedded within the brush filaments 14. In other words, if such a smaller coil spring were used, the brush filaments 14 might extend both within the coil spring and along the outer surface of the coil spring. Using an embodiment of the invention as described above, with a wet-brush electrode and a copper coil spring, linear lesions 26-46 mm long and 3-4 mm deep were created in 60 seconds at 30 Watts of power and 12 ml/minute of saline flow.

What is claimed is:

1. A booted, spring-tip, flexible electrode catheter comprising
    an inner sheath having an inner sheath distal end and defining an inner sheath lumen, wherein said inner sheath distal end supports a mechanical interface;
    an intermediate sheath having an intermediate sheath distal portion and defining an intermediate sheath lumen;
    an outer sheath having an outer sheath distal end and defining an outer sheath lumen;
    a flexible electrode supported by said mechanical interface;
    a spring at said inner sheath distal end, wherein said spring has a distal portion, and wherein said spring enshrouds at least a portion of said flexible electrode; and
    a flexible boot having a flexible boot distal edge, wherein said flexible boot covers said distal portion of said spring, and wherein said flexible electrode extends from said flexible boot distal edge.

2. The booted, spring-tip, flexible electrode catheter of claim 1 further comprising
    a lubricious outer wall that envelopes said outer sheath, wherein said lubricious outer wall terminates at a lubricious outer wall distal edge adjacent to said outer sheath distal end; and
    wherein said flexible boot extends from an annular juncture with said lubricious outer wall distal edge to a ring of contact with said flexible electrode at said flexible boot distal edge.

3. The booted, spring-tip, flexible electrode catheter of claim 1 further comprising a conductor having a contact portion in electrical contact with said flexible electrode.

4. The booted, spring-tip, flexible electrode catheter of claim 3, wherein said contact portion of said conductor is wrapped around an outer surface of said flexible electrode.

5. The booted, spring-tip, flexible electrode catheter of claim 3, wherein said contact portion of said conductor comprises at least one conductive loop wrapped around an outer surface of said flexible electrode.

6. The booted, spring-tip, flexible electrode catheter of claim 5, wherein said spring further comprises a proximal end, and wherein said at least one conductive loop is located between said inner sheath distal end and said proximal end of said spring.

7. The booted, spring-tip, flexible electrode catheter of claim 5, wherein said spring is a coil spring comprising a plurality of coils including proximal coils, and wherein said at least one conductive loop comprises a plurality of conductive loops wrapped among said proximal coils.

8. The booted, spring-tip, flexible electrode catheter of claim 5, wherein said intermediate sheath distal portion extends adjacent to an outer surface of said at least one conductive loop.

9. The booted, spring-tip, flexible electrode catheter of claim 8, wherein said spring further comprises a proximal portion, and wherein said intermediate sheath distal portion also supports said proximal portion of said spring.

10. The booted, spring-tip, flexible electrode catheter of claim 1, wherein said outer sheath circumscribes and is radially offset from said intermediate sheath, thereby forming an annular channel between said outer sheath and said intermediate sheath, and wherein said annular channel is adapted to introduce fluid to said flexible electrode.

11. The booted, spring-tip, flexible electrode catheter of claim 10, wherein said intermediate sheath further comprises an intermediate sheath distal end that is longitudinally inset from said outer sheath distal end, thereby forming an annular fluid jacket between an inner surface of said outer sheath and an outer surface of said flexible electrode, and wherein said annular fluid jacket is in fluid communication with said annular channel.

12. The booted, spring-tip, flexible electrode catheter of claim 1 further comprising
    at least one diagnostic sensor adjacent to said outer sheath distal end; and
    at least one diagnostic lead in communication with said at least one diagnostic sensor.

13. A spring-tip, flexible electrode catheter comprising
    a catheter sheath having a distal end;
    a flexible electrode extending from said distal end of said catheter sheath, wherein said flexible electrode is electrically conductive, wherein said flexible electrode is a brush electrode comprising a plurality of flexible filaments, and wherein said plurality of flexible filaments of said brush electrode comprises conductive filaments and nonconductive filaments;
    a spring at said distal end of said catheter sheath, wherein said spring enshrouds at least a portion of said flexible electrode; and
    a primary conductor operatively connected to said flexible electrode.

14. A spring-tip, flexible electrode catheter comprising
a catheter sheath having a distal end, wherein said catheter sheath defines a catheter lumen;
a flexible electrode extending from said distal end of said catheter sheath; and
a spring at said distal end of said catheter sheath, wherein said spring enshrouds at least a portion of said flexible electrode, wherein said spring comprises an embedded spring having an embedded portion and an exposed portion, wherein said embedded portion of said embedded spring extends within said catheter lumen, wherein said exposed portion of said embedded spring extends from said distal end of said catheter sheath, wherein said flexible electrode comprises an embedded portion and an exposed portion, and wherein said embedded portion of said flexible electrode extends within said embedded portion of said embedded spring.

15. The spring-tip, flexible electrode catheter of claim 14, wherein said exposed portion of said embedded spring has a distal end, and wherein said exposed portion of said flexible electrode extends distally past said distal end of said exposed portion of said embedded spring.

16. A spring-tip, flexible electrode catheter comprising
a catheter sheath having a distal end;
a flexible electrode extending from said distal end of said catheter sheath, wherein said flexible electrode comprises an embedded portion and an exposed portion, and wherein said exposed portion extends from said distal end of said catheter sheath a first distance; and
a spring at said distal end of said catheter sheath, wherein said spring enshrouds at least a portion of said flexible electrode, and wherein said spring has
 a proximal end,
 a distal end,
 an uncompressed length from said distal end of said catheter sheath to said distal end of said spring measured when said spring is fully uncompressed, and
 a compressed length from said distal end of said catheter sheath to said distal end of said spring measured when said spring is fully compressed; and
wherein said first distance is greater than said uncompressed length.

17. A spring-tip, flexible electrode catheter comprising
a catheter sheath having a distal end;
a flexible electrode extending from said distal end of said catheter sheath;
a spring at said distal end of said catheter sheath, wherein said spring enshrouds at least a portion of said flexible electrode; and
a nipple around said spring at said distal end of said catheter sheath.

18. The spring-tip, flexible electrode catheter of claim 17, wherein said flexible electrode comprises a plurality of flexible brush filaments and at least one hollow filament, wherein said at least one hollow filament comprises an open distal end embedded among, and adapted to deliver fluid to, said plurality of flexible brush filaments.

* * * * *